(12) United States Patent
Sandahl

(10) Patent No.: US 10,034,782 B2
(45) Date of Patent: Jul. 31, 2018

(54) VARIABLE STIFFNESS PROSTHETIC FOOT

(71) Applicant: Össur hf, Reykjavik (IS)

(72) Inventor: David Sandahl, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/858,693

(22) Filed: Sep. 18, 2015

(65) Prior Publication Data

US 2016/0081821 A1 Mar. 24, 2016

Related U.S. Application Data

(60) Provisional application No. 62/053,000, filed on Sep. 19, 2014.

(51) Int. Cl.
*A61F 2/66* (2006.01)
*A61F 2/50* (2006.01)

(52) U.S. Cl.
CPC .......... *A61F 2/66* (2013.01); *A61F 2002/503* (2013.01); *A61F 2002/665* (2013.01); *A61F 2002/6614* (2013.01); *A61F 2002/6621* (2013.01); *A61F 2002/6628* (2013.01); *A61F 2002/6642* (2013.01); *A61F 2002/6657* (2013.01);
(Continued)

(58) Field of Classification Search
CPC ................ A61F 2/66; A61F 2002/6657; A61F 2002/6664; A61F 2002/6678
See application file for complete search history.

(56) References Cited

U.S. PATENT DOCUMENTS 4,413,360 A 11/1983 Lamb et al.
4,764,172 A 8/1988 McCoy
(Continued)

FOREIGN PATENT DOCUMENTS

EP 0606383 B1 3/1997
EP 0729326 B1 11/2001
(Continued)

OTHER PUBLICATIONS

International Search Report and Written Opinion in corresponding International Application No. PCT/US2015/051077, dated Dec. 28, 2015, in 7 pages.
(Continued)

*Primary Examiner* — Bruce E Snow
(74) *Attorney, Agent, or Firm* — Knobbe, Martens, Olson & Bear, LLP

(57) ABSTRACT

Prosthetic feet that provide for variable and adjustable stiffness are provided. A foot element can include a tongue portion defined or formed by a slot in the foot element that at least partially separates the tongue portion from a remainder of the foot element. The tongue portion can be operably connected to the remainder of the foot member to increase the stiffness of the foot member or operably disconnected from the remainder of the foot member to increase the flexibility of the foot member. The prosthetic foot further includes a mechanism for adjusting whether the tongue portion is operably connected or disconnected from the remainder of the foot member. The mechanism can be selectively actuated to adjust the stiffness of the foot element in dorsiflexion and/or plantarflexion and/or to adjust the degree to which the tongue portion is allowed to flex relative to the remainder of the foot member.

23 Claims, 19 Drawing Sheets

(52) U.S. Cl.
CPC ............... *A61F 2002/6664* (2013.01); *A61F 2002/6671* (2013.01); *A61F 2002/6678* (2013.01)

(56) References Cited

U.S. PATENT DOCUMENTS

| | | | |
|---|---|---|---|
| 4,959,073 | A | 9/1990 | Merlette |
| 5,112,356 | A | 5/1992 | Harris et al. |
| 5,139,525 | A | 8/1992 | Kristinsson |
| 5,376,141 | A | 12/1994 | Phillips |
| 5,571,212 | A | 11/1996 | Cornelius |
| 5,695,527 | A | 12/1997 | Allen |
| 5,725,598 | A | 3/1998 | Phillips |
| 5,944,760 | A * | 8/1999 | Christensen ............ A61F 2/66 623/52 |
| 6,071,313 | A * | 6/2000 | Phillips ............ A61F 2/66 623/55 |
| 6,261,324 | B1 | 7/2001 | Merlette |
| 6,402,790 | B1 | 6/2002 | Celebi |
| 6,406,500 | B1 | 6/2002 | Phillips |
| 6,767,370 | B1 | 7/2004 | Mosler et al. |
| 6,855,170 | B2 | 2/2005 | Gramnäs |
| 7,060,104 | B2 | 6/2006 | Phillips |
| 7,618,464 | B2 | 11/2009 | Christensen |
| 7,686,848 | B2 | 3/2010 | Christensen |
| 7,708,784 | B2 | 5/2010 | Townsend et al. |
| 7,727,285 | B2 | 6/2010 | Christensen et al. |
| 7,833,287 | B2 | 11/2010 | Doddroe et al. |
| 7,879,110 | B2 | 2/2011 | Phillips |
| 7,942,935 | B2 | 5/2011 | Iversen et al. |
| 8,070,829 | B2 | 12/2011 | Townsend et al. |
| 8,118,879 | B2 | 2/2012 | Wilson |
| 8,298,294 | B2 | 10/2012 | Kaltenborn et al. |
| 8,366,790 | B2 | 2/2013 | Curtis |
| 8,551,184 | B1 | 10/2013 | Herr |
| 9,561,118 | B2 | 2/2017 | Clausen et al. |
| 2002/0077706 | A1 * | 6/2002 | Phillips ............ A61F 2/66 623/52 |
| 2005/0171618 | A1 * | 8/2005 | Christensen ............ A61F 2/66 623/56 |
| 2006/0212131 | A1 | 9/2006 | Curtis |
| 2007/0073410 | A1 | 3/2007 | Raugel |
| 2008/0004718 | A1 | 1/2008 | Mosler |
| 2008/0188950 | A1 | 8/2008 | Fleury et al. |
| 2008/0306612 | A1 | 12/2008 | Mosler |
| 2009/0012630 | A1 | 1/2009 | Mosler et al. |
| 2010/0030342 | A1 | 2/2010 | Oddsson et al. |
| 2010/0305716 | A1 | 12/2010 | Pusch et al. |
| 2012/0010730 | A1 | 1/2012 | Lecomte et al. |
| 2012/0209405 | A1 | 8/2012 | Herr et al. |
| 2013/0006386 | A1 | 1/2013 | Hansen et al. |
| 2013/0060349 | A1 | 3/2013 | Thorsteinsson et al. |
| 2013/0066439 | A1 | 3/2013 | Zamora et al. |
| 2013/0085581 | A1 | 4/2013 | Lecomte et al. |
| 2013/0144403 | A1 | 6/2013 | Lecomte et al. |
| 2013/0261767 | A1 | 10/2013 | Kranner et al. |
| 2013/0331953 | A1 | 12/2013 | Doddroe et al. |
| 2014/0058531 | A1 | 2/2014 | Clausen et al. |
| 2014/0067086 | A1 | 3/2014 | Moser et al. |
| 2014/0074243 | A1 | 3/2014 | Holgate |

FOREIGN PATENT DOCUMENTS

| | | |
|---|---|---|
| EP | 1187583 B1 | 7/2005 |
| EP | 1670399 B1 | 9/2009 |
| EP | 2522311 A2 | 11/2012 |
| EP | 2620126 A1 | 7/2013 |
| EP | 2663264 B1 | 9/2015 |
| WO | WO 2003/071993 A1 | 9/2003 |
| WO | WO 2006/081231 A1 | 8/2006 |
| WO | WO 2007/041527 A2 | 4/2007 |
| WO | WO 2012/009319 A2 | 1/2012 |
| WO | WO 2012/177125 A1 | 12/2012 |
| WO | WO 2013/017856 A1 | 2/2013 |
| WO | WO 2013/049852 A2 | 4/2013 |
| WO | WO 2013/055462 A1 | 4/2013 |

OTHER PUBLICATIONS

Extended Search Report in corresponding European Patent Application No. 15842555.3, dated May 2, 2018, in 5 pages.

* cited by examiner

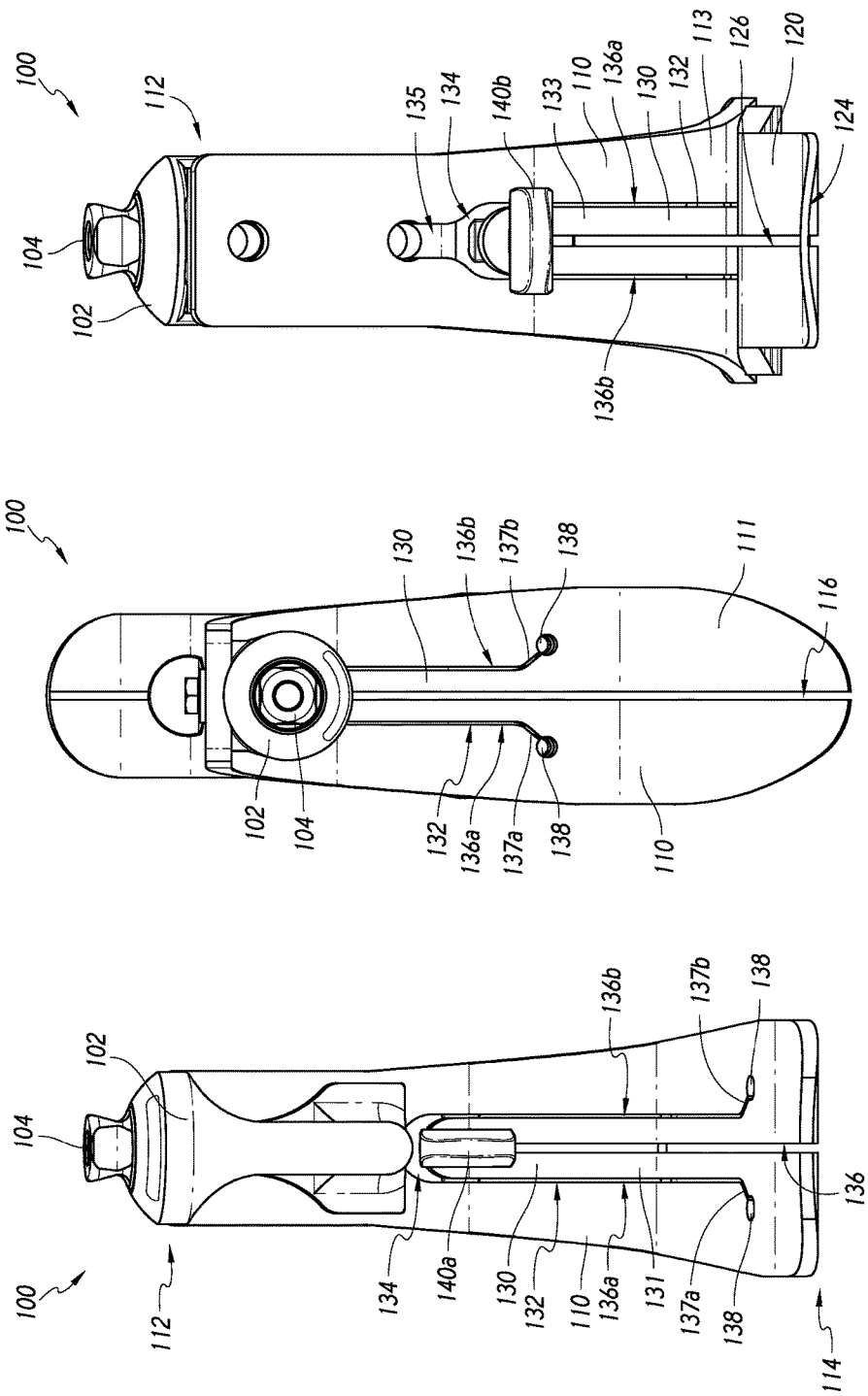

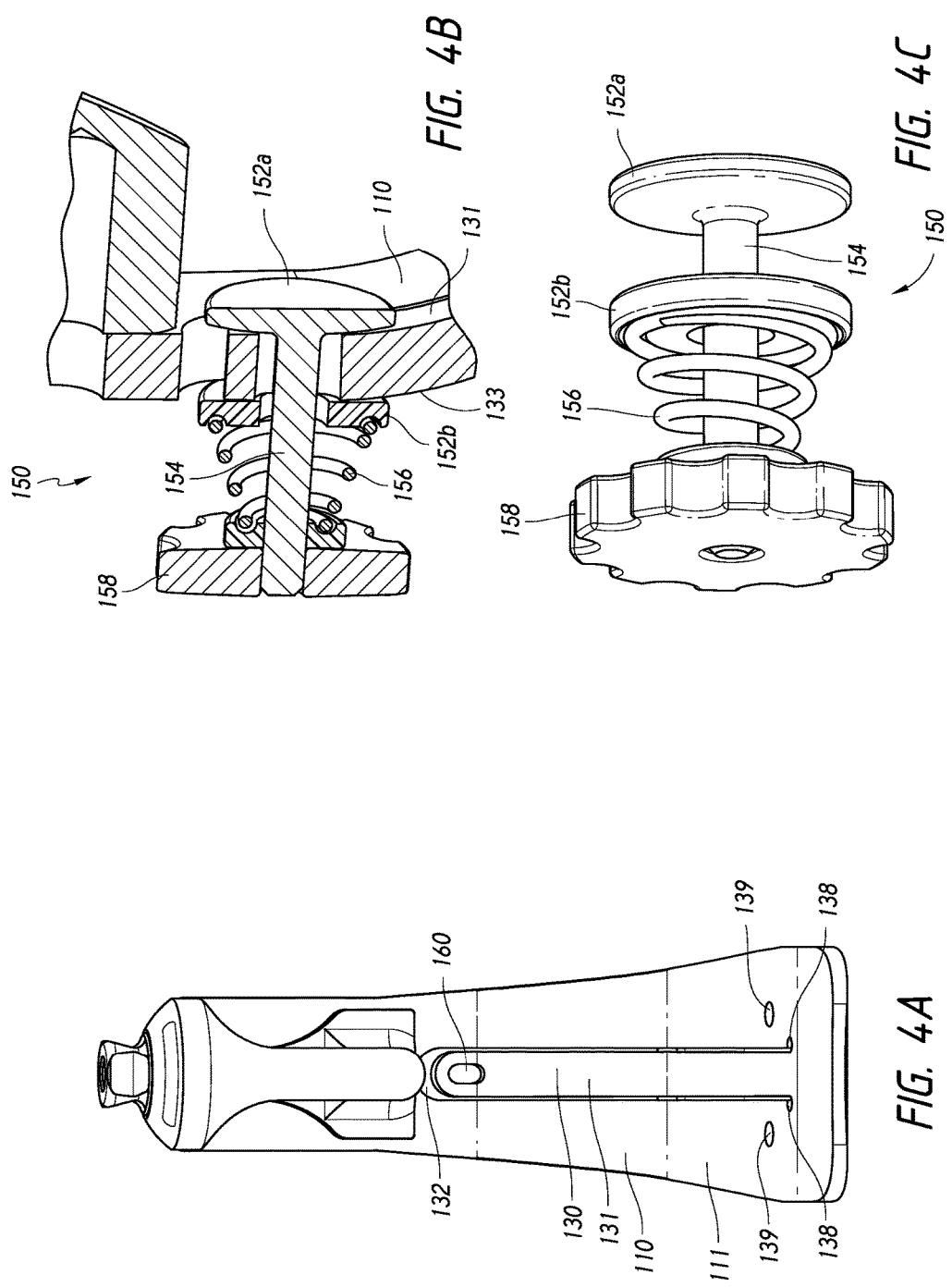

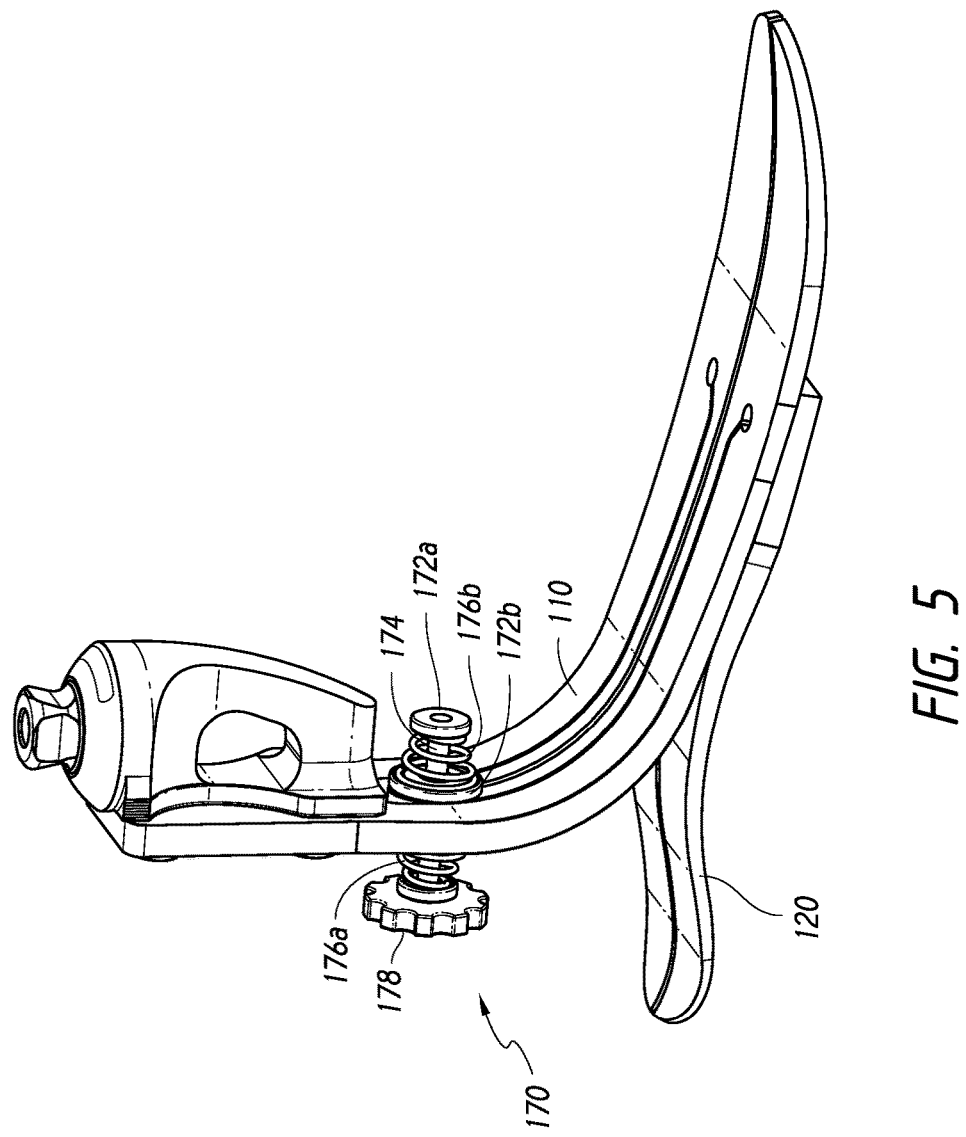

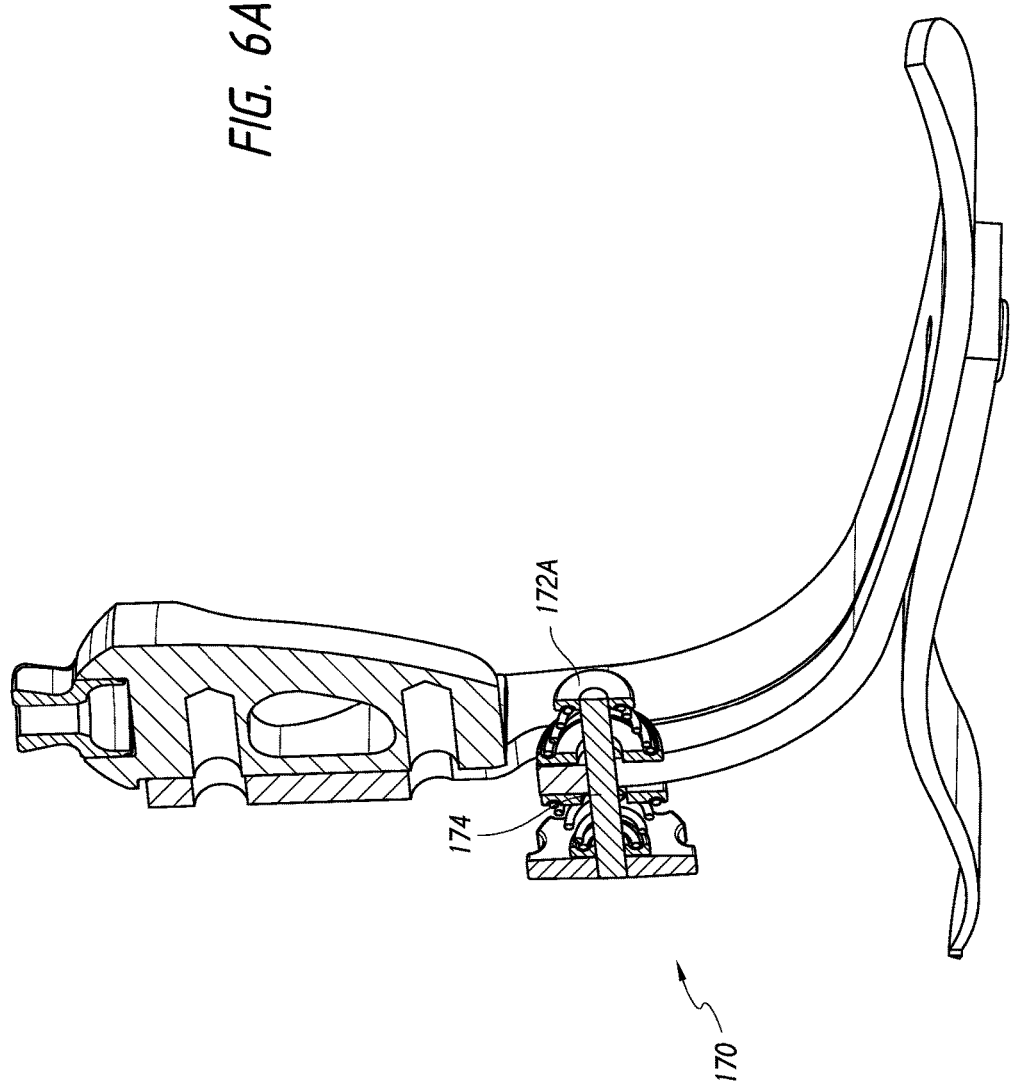

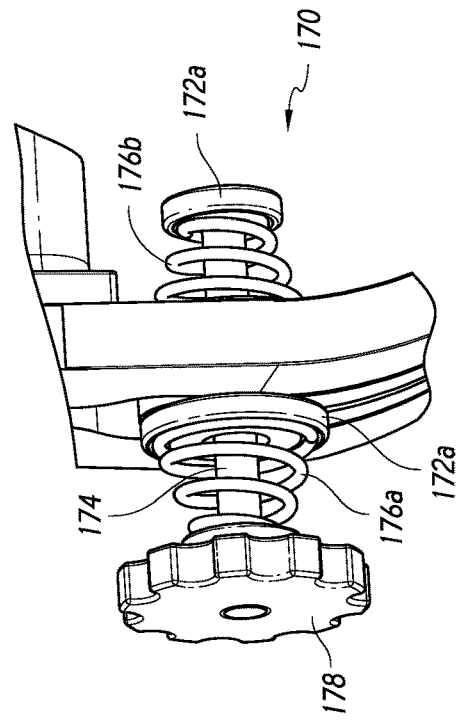
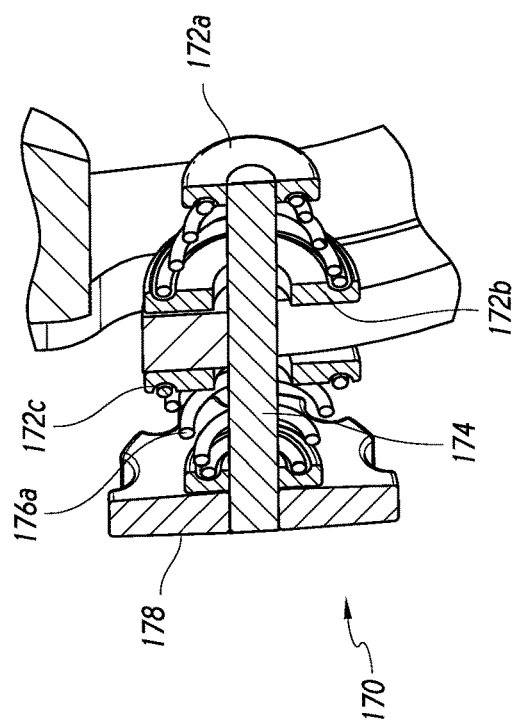
FIG. 6C
FIG. 6B

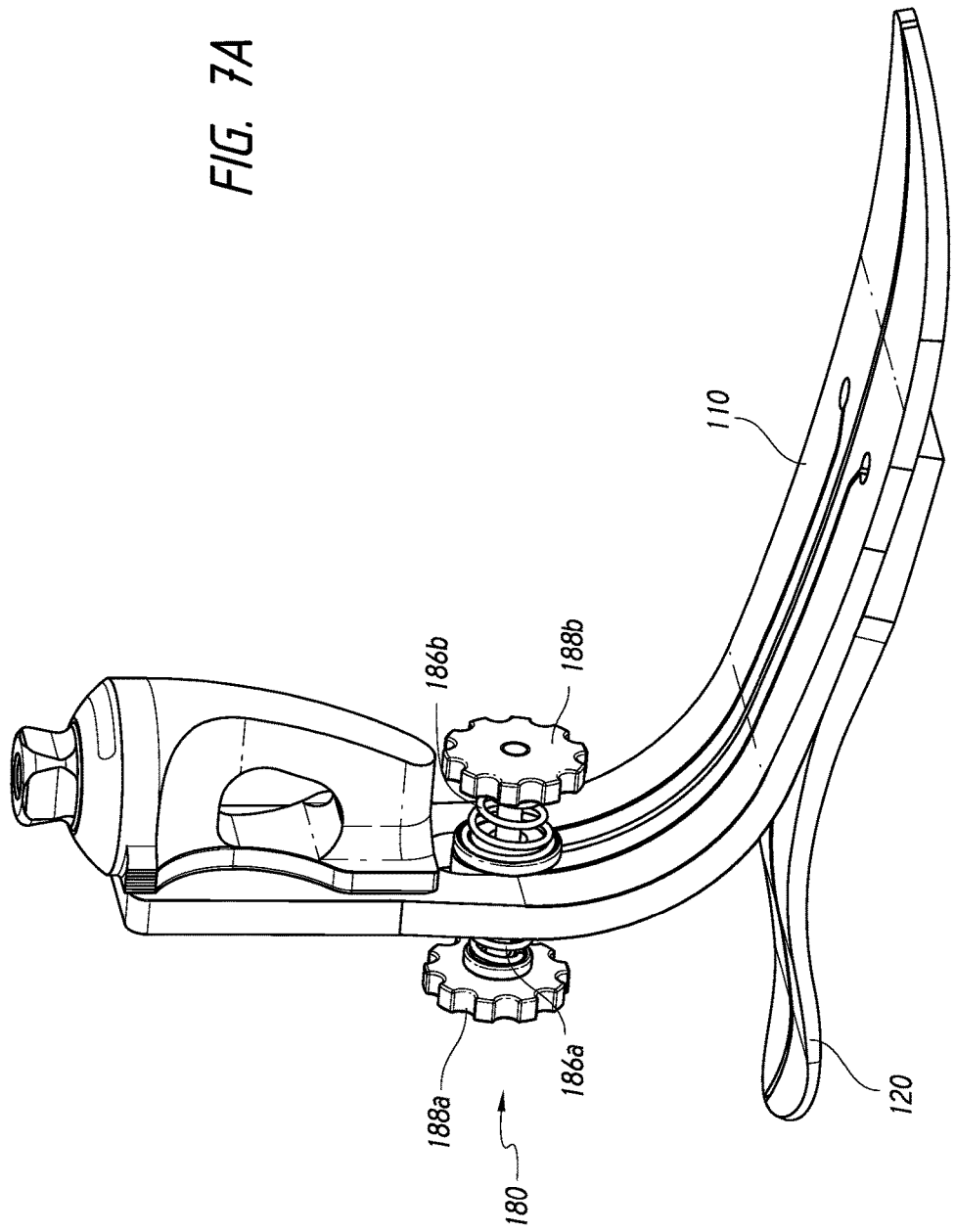

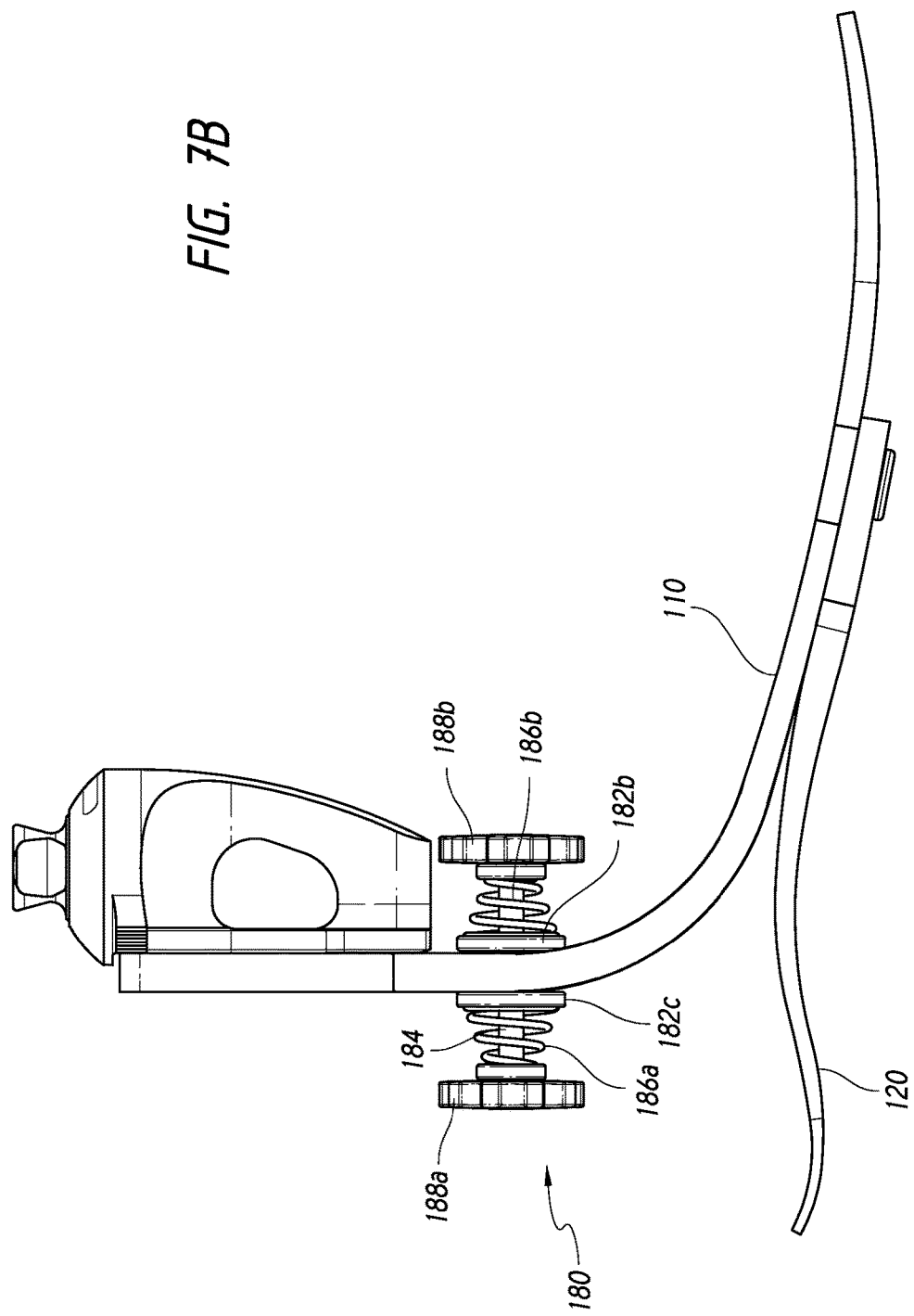

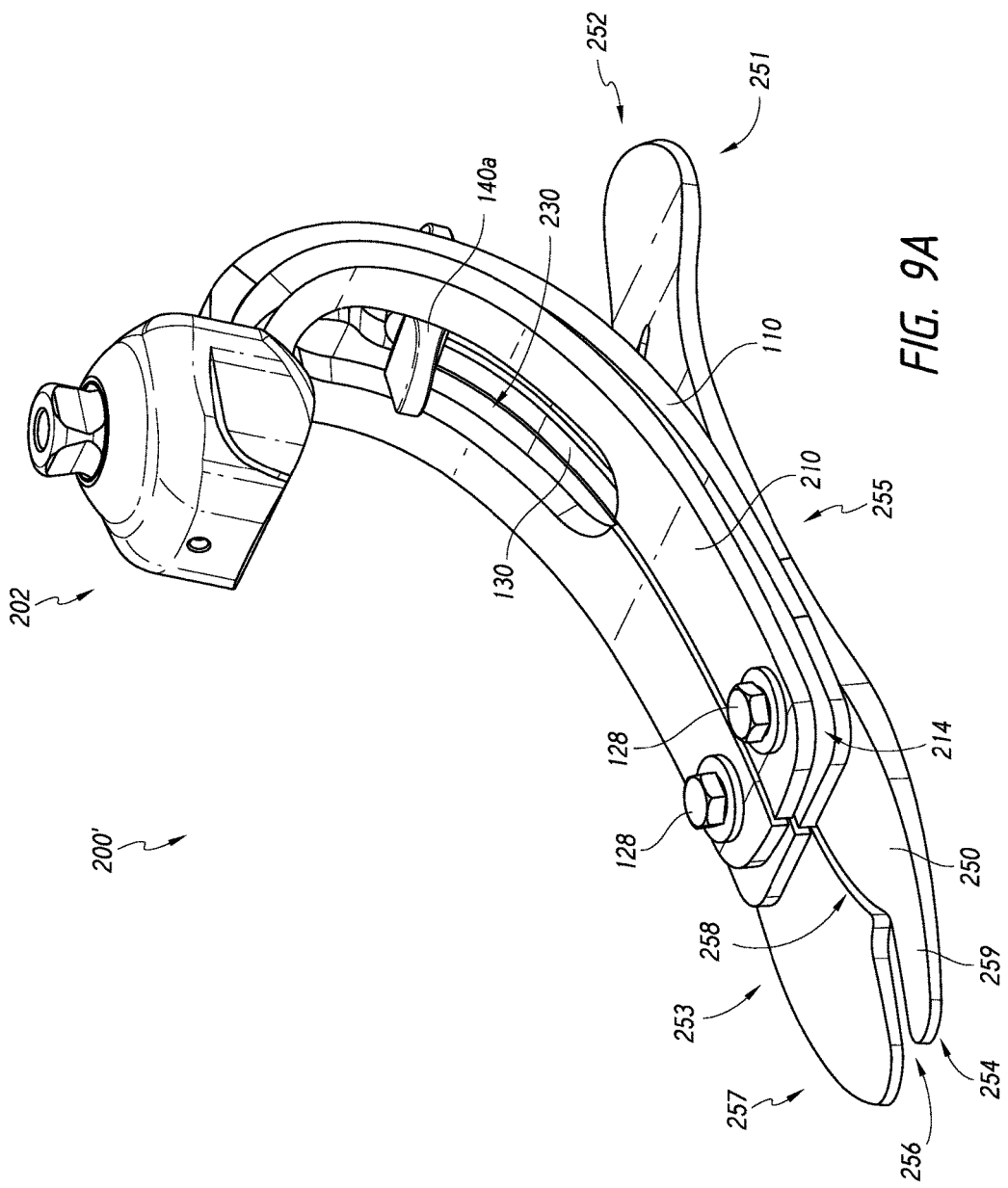

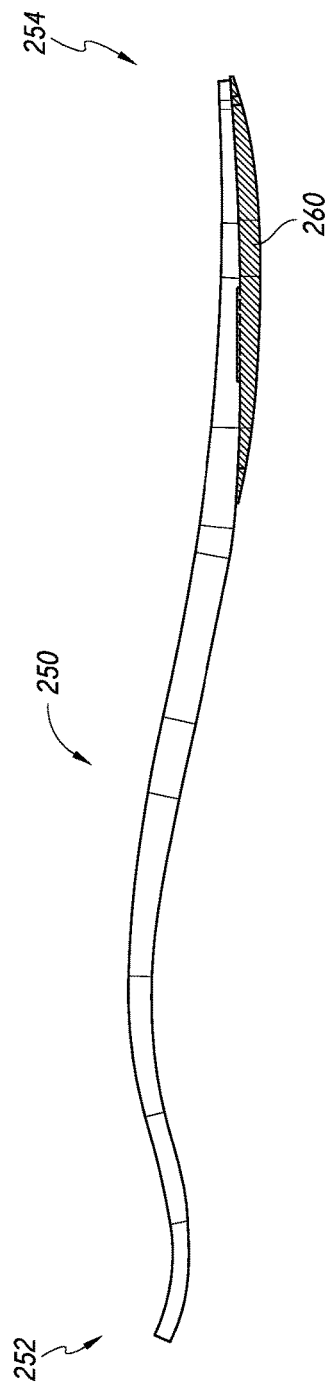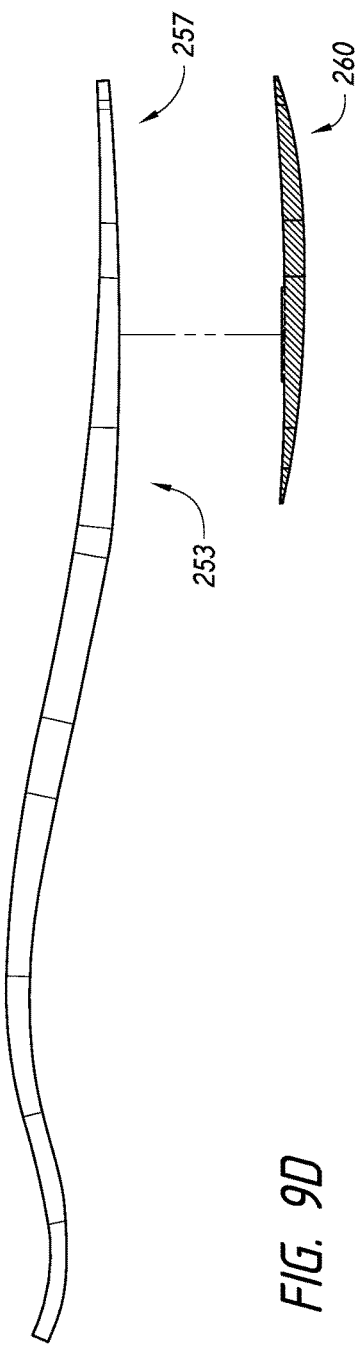
FIG. 9C
FIG. 9D

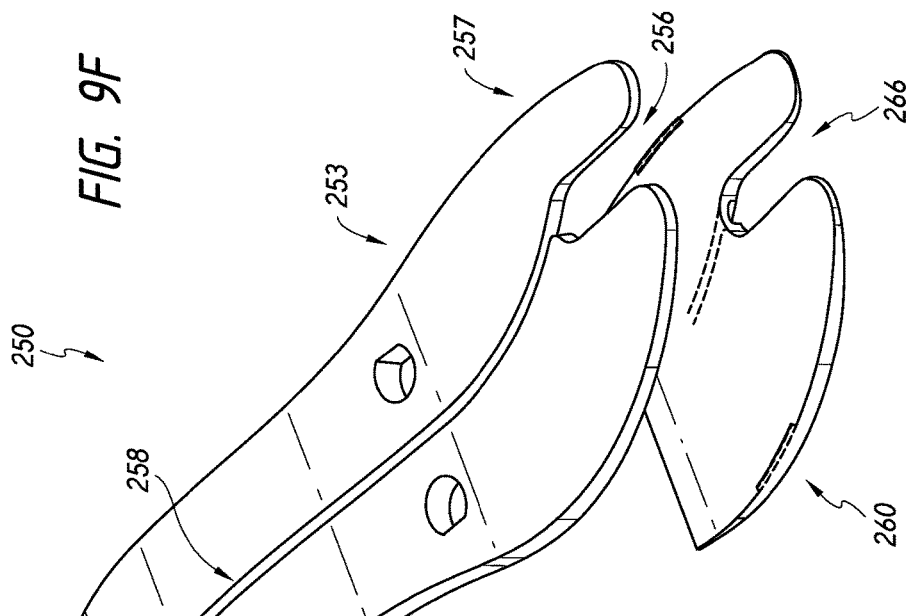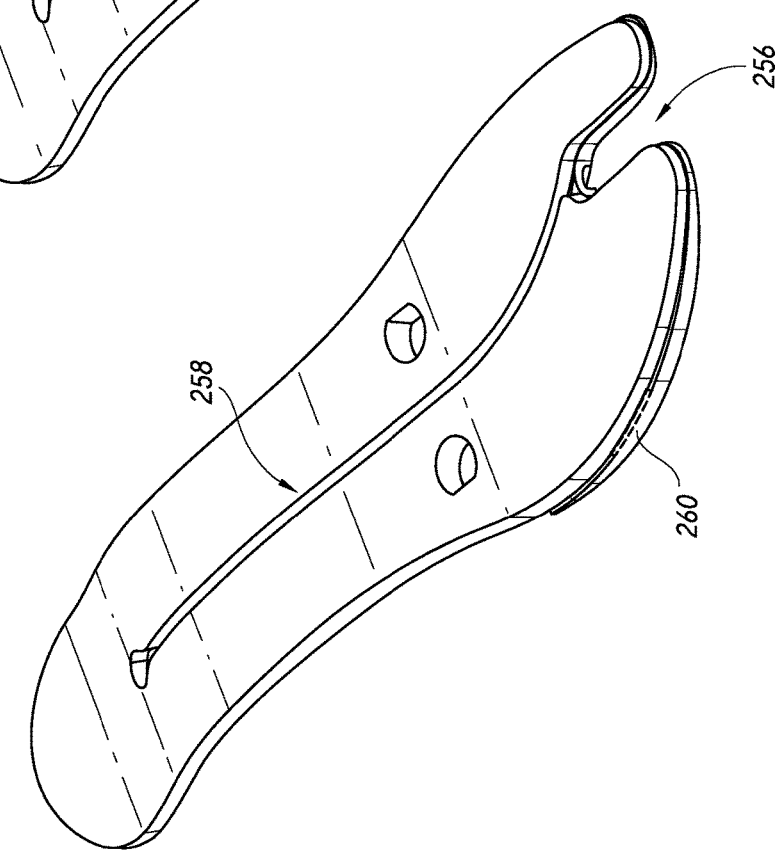

VARIABLE STIFFNESS PROSTHETIC FOOT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 62/053,000, filed Sep. 19, 2014, the entirety of which is hereby incorporated by reference herein and should be considered part of this specification.

BACKGROUND

Field

The present disclosure relates generally to prosthetic feet. In some embodiments, the present disclosure relates more specifically to prosthetic feet having adjustable stiffness and flexibility characteristics.

Description of the Related Art

Various types of prosthetic feet are available as substitutes for natural human feet. Such feet can be made of various materials having various stiffness or flexibility characteristics. Existing feet generally have a predetermined stiffness level as defined by, for example, the material(s) making up the foot, thickness of the foot plate, etc.

SUMMARY

Some aspects of the present disclosure provide for prosthetic feet having adjustable stiffness characteristics.

In some embodiments, a prosthetic foot includes an elongate foot element extending from a proximal end to a toe end. The foot element includes a tongue portion defined by a generally U-shaped cutout in the foot element. The tongue portion is configured to flex at least partially independently of a remainder of the foot element. The prosthetic foot further includes a mechanism configured to be selectively actuated to operatively connect or operatively disconnect the tongue portion from the remainder of the foot element. When the tongue portion is operatively connected to the remainder of the foot element, the foot element exhibits relatively greater stiffness, and when the tongue portion is operatively disconnected from the remainder of the foot element, the foot element exhibits relatively lower stiffness.

The mechanism can be configured to be selectively actuated to adjust the stiffness of the foot element in one or both of plantarflexion and dorsiflexion. In some embodiments, the mechanism includes first and second engagement members coupled to the tongue portion. The first engagement member is disposed on a front side of the foot element and the second engagement member is disposed on a back side of the foot element. The first engagement member is configured to be actuated to selectively operatively connect or operatively disconnect the tongue portion from the remainder of the foot element in dorsiflexion, and the second engagement member is configured to be actuated to selectively operatively connect or operatively disconnect the tongue portion from the remainder of the foot element in plantarflexion.

In some embodiments, the mechanism includes a shaft extending through an aperture near a proximal end of the tongue portion, a flange at a first end of the shaft, an adjustment knob at a second end of the shaft, a washer slidably disposed on the shaft between the adjustment knob and the foot element, and a spring disposed around the shaft. The spring extends between and is coupled to the adjustment knob and the washer. The tongue portion is disposed between the flange and the washer, and the knob is selectively adjustable to vary a stiffness of the foot element. In some embodiments, the mechanism further includes a second washer and a second spring. The second spring is interposed about the shaft between the second washer and the flange, and the tongue portion is interposed between the washer and the second washer.

In some embodiments, the mechanism includes a shaft extending through an aperture near a proximal end of the tongue portion, a first adjustment knob at a first end of the shaft, a first washer slidably disposed on the shaft between the first adjustment knob and a rear side of the foot element, a spring disposed around the shaft and extending between and coupled to the first adjustment knob and the first washer, a second adjustment knob at a second end of the shaft, a second washer slidably disposed on the shaft between the second adjustment knob and a front side of the foot element, and a second spring disposed around the shaft and extending between and coupled to the second adjustment knob and the second washer. The first and second knobs are selectively adjustable to respectively and independently vary a stiffness of the foot element in plantarflexion and dorsiflexion.

In some embodiments, a prosthetic foot includes an elongate foot element extending from a proximal end to a toe end. The foot element includes a tongue portion defined by a generally U-shaped cutout in the foot element. The tongue portion is configured to flex at least partially independently of a remainder of the foot element. The prosthetic foot further includes means coupled to the tongue portion for selectively adjusting a stiffness of the elongate foot element during one or both of the dorsiflexion and plantarflexion between at least two different stiffness levels.

In some embodiments, the means is configured to independently vary a stiffness of the foot element in dorsiflexion and plantarflexion. In some embodiments, the means selectively operatively connects the tongue portion to or from the remainder of the foot element to thereby adjust the stiffness of the elongate foot element during one or both of dorsiflexion and plantarflexion. When the tongue portion is operatively connected to the remainder of the foot element, the foot element exhibits relatively greater stiffness, and when the tongue portion is operatively disconnected from the remainder of the foot element, the foot element exhibits relatively lower stiffness.

According to one aspect of the present disclosure, there is provided a prosthetic foot that includes an elongate foot element extending from a proximal end to a distal end, the foot element comprising a tongue portion defined by a slot in the foot element that at least partially separates the tongue portion from a remainder of the elongate foot element. The prosthetic foot further includes a mechanism configured to be selectively actuated to operatively connect or operatively disconnect the tongue portion from the remainder of the foot element, wherein when the tongue portion is operatively connected to the remainder of the foot element the foot element exhibits relatively greater stiffness, and when the tongue portion is operatively disconnected from the remainder of the foot element the foot element exhibits relatively lower stiffness.

The prosthetic foot may be arranged such that the mechanism is configured to be selectively actuated to adjust the stiffness of the foot element in one or both of plantarflexion and dorsiflexion. The prosthetic foot may be arranged such that the mechanism further comprises first and second engagement members coupled to the tongue portion, the first engagement member disposed on a front side of the foot element and the second engagement member disposed on a back side of the foot element, wherein the first engagement member is configured to be actuated to selectively operatively connect or operatively disconnect the tongue portion from the remainder of the foot element in dorsiflexion, and wherein the second engagement member is configured to be actuated to selectively operatively connect or operatively disconnect the tongue portion from the remainder of the foot element in plantarflexion.

The prosthetic foot may be arranged such that the mechanism comprises a shaft extending through an aperture near a proximal end of the tongue portion, a flange at a first end of the shaft, an adjustment knob at a second end of the shaft, a washer slidably disposed on the shaft between the adjustment knob and the foot element, and a spring disposed around the shaft and extending between and coupled to the adjustment knob and the washer, wherein the tongue portion is disposed between the flange and the washer and wherein the knob is selectively adjustable to vary a compression of the spring to adjust a stiffness of the foot element. The prosthetic foot may be arranged such that the mechanism further comprises a second washer and a second spring, the second spring interposed about the shaft between the second washer and the flange, and wherein the tongue portion is interposed between the washer and the second washer.

The prosthetic foot may be arranged such that the mechanism comprises a shaft extending through an aperture near a proximal end of the tongue portion, a first adjustment knob at a first end of the shaft, a first washer slidably disposed on the shaft between the first adjustment knob and a rear side of the foot element, and a spring disposed around the shaft and extending between and coupled to the first adjustment knob and the first washer, a second adjustment knob at a second end of the shaft, a second washer slidably disposed on the shaft between the second adjustment knob and a front side of the foot element, and a second spring disposed around the shaft and extending between and coupled to the second adjustment knob and the second washer, wherein the tongue portion is disposed between the first and second washers, and wherein the first and second knobs are selectively adjustable to respectively and independently vary a stiffness of the foot element in plantarflexion and dorsiflexion.

The prosthetic foot may be arranged such that when the tongue portion is operatively connected to the remainder of the foot element the tongue portion flexes with the remainder of the foot element, and when the tongue portion is operatively disconnected from the remainder of the foot element the tongue portion flexes at least partially independently of the remainder of the foot element. The prosthetic foot may further be arranged such that the tongue portion is configured to flex with the remainder of the foot element during one of plantarflexion and dorsiflexion and configured to flex at least partially independently of the remainder of the foot element during the other of plantarflexion and dorsiflexion.

The prosthetic foot may further include an adapter coupled to the foot element proximate to the proximal end.

The prosthetic foot may be arranged such that the distal end of the foot element defines a toe portion.

The prosthetic foot may further include a second foot element disposed below the foot element. The prosthetic foot may further be arranged such that the second foot element extends from a heel end to a toe end of the prosthetic foot. Alternatively, the prosthetic foot may be arranged such that the second foot element is a heel plate that extends from a heel end of the prosthetic foot to a location proximal of the distal end of the foot element.

According to another aspect of the present disclosure, a prosthetic foot is provided that includes an elongate foot element extending from a proximal end to a distal end, the foot element comprising a tongue portion defined by a slot in the foot element that at least partially separates the tongue portion from a remainder of the elongate foot element. The prosthetic foot also includes means for selectively coupling the tongue portion with the remainder of the foot element for selectively adjusting a stiffness of the elongate foot element during one or both of dorsiflexion and plantarflexion between at least two different stiffness levels.

The prosthetic foot may be arranged such that the means is configured to independently vary a stiffness of the foot element in dorsiflexion and plantarflexion.

The prosthetic foot may be arranged such that the means selectively operatively connects or operatively disconnects the tongue portion from the remainder of the foot element to thereby adjust the stiffness of the elongate foot element during one or both of dorsiflexion and plantarflexion, wherein when the tongue portion is operatively connected to the remainder of the foot element, the foot element exhibits relatively greater stiffness, and when the tongue portion is operatively disconnected from the remainder of the foot element, the foot element exhibits relatively lower stiffness.

The prosthetic foot may be arranged such that when the tongue portion is coupled to the remainder of the foot element the tongue portion flexes with the remainder of the foot element, and when the tongue portion is not coupled to the remainder of the foot element the tongue portion flexes at least partially independently of the remainder of the foot element. The prosthetic foot may further be arranged such that the tongue portion is configured to flex with the remainder of the foot element during one of plantarflexion and dorsiflexion and configured to flex at least partially independently of the remainder of the foot element during the other of plantarflexion and dorsiflexion.

According to another aspect of the present disclosure, a prosthetic foot is provided that includes a first elongate foot element and a second foot element. The first elongate foot element extends from a proximal end to a distal end and comprises a tongue portion defined by a slot in the foot element that at least partially separates the tongue portion from a remainder of the first elongate foot element. The second foot element is disposed below and coupled to the first elongate foot element, and the distal end of the first elongate foot element is positioned proximal of the toe end of the second foot element. The prosthetic foot also includes a mechanism configured to be selectively actuated to operatively connect or operatively disconnect the tongue portion from the remainder of the first elongate foot element, wherein when the tongue portion is operatively connected to the remainder of the first elongate foot element the first elongate foot element exhibits relatively greater stiffness, and when the tongue portion is operatively disconnected from the remainder of the first elongate foot element the foot element exhibits relatively lower stiffness.

The prosthetic foot can be arranged such that the first elongate foot element is generally C-shaped.

The prosthetic foot can be arranged such that the mechanism comprises at least one tab engagement member and wherein the tongue portion is operatively connected to the remainder of the first elongate foot element when the tab engagement member is positioned in a first orientation and the tongue portion is operatively disconnected from the remainder of the first elongate foot element when the tab engagement member is positioned in a second orientation. The prosthetic foot may further be arranged such that the at least one tab engagement member comprises two tab engagement members, a first tab engagement member disposed on a front side of the first elongate foot element and a second tab engagement member disposed on a back side of the first elongate foot element.

The prosthetic foot can be arranged such that the tongue portion is operatively connected to the remainder of the first elongate foot element the tongue portion flexes with the remainder of the first elongate foot element, and when the tongue portion is operatively disconnected from the remainder of the first elongate foot element the tongue portion flexes at least partially independently of the remainder of the first elongate foot element. The prosthetic foot may further be arranged such that the tongue portion is configured to flex with the remainder of the first elongate foot element during one of plantarflexion and dorsiflexion and configured to flex at least partially independently of the remainder of the first elongate foot element during the other of plantarflexion and dorsiflexion.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 1A illustrates a front view of an example embodiment of a prosthetic foot having a mechanism for adjusting stiffness;

FIG. 1B illustrates a top view of the prosthetic foot of FIG. 1A;

FIG. 1C illustrates a rear view of the prosthetic foot of FIGS. 1A and 1B;

FIG. 4A illustrates the foot member and attachment adapter of the prosthetic foot of FIG. 3;

FIG. 4B illustrates a cross-sectional view of the spring mechanism of FIG. 3 coupled to the foot member of FIG. 4A;

FIG. 4C illustrates the spring mechanism of FIGS. 3 and 4B;

FIG. 5 illustrates an example embodiment of a prosthetic foot having a dual spring mechanism for adjusting stiffness;

FIG. 6A illustrates a cross-sectional view of the prosthetic foot of FIG. 5;

FIG. 6B illustrates a cross-sectional view of the spring mechanism coupled to the foot member of FIGS. 5 and 6A;

FIG. 6C illustrates a close-up view of the spring mechanism coupled to the foot member of FIGS. 5-6B;

FIG. 7A illustrates a perspective view of an example embodiment of a prosthetic foot having an alternative dual spring mechanism for adjusting stiffness;

FIG. 7B illustrates a side view of the prosthetic foot of FIG. 7A;

FIG. 9A illustrates an another example embodiment of a prosthetic foot including the mechanism for adjusting stiffness of FIGS. 1A-3D;

FIGS. 9C-9F illustrate an example embodiment of a foot element including a drop-toe portion.

DETAILED DESCRIPTION

Figure 2A:
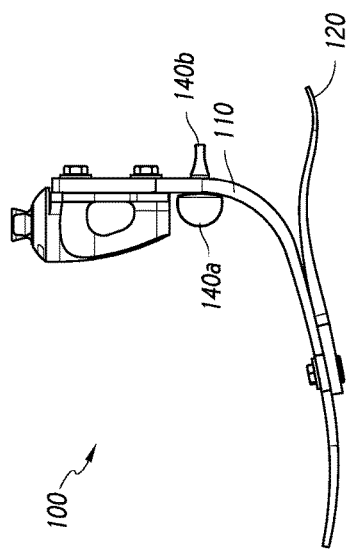
FIGS. 2A-2D illustrate the prosthetic foot of FIGS. 1A-1C with the mechanism for adjusting stiffness in various configurations.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

The present disclosure provides various examples of prosthetic feet and features for prosthetic feet that advantageously allow for adjustment of the stiffness and/or flexibility of the feet. Prosthetic feet according to the present disclosure can include an elongate, plate-like foot member having a mechanism for variable or configurable stiffness in the foot member. The prosthetic feet and features shown and described herein advantageously allow for customized independent control over the flexibility of the foot in either or both of dorsiflexion and plantarflexion.

FIGS. 1A-1C illustrate front, top, and rear view, respectively, of an example embodiment of a prosthetic foot 100 including features that allow for adjustable stiffness. The foot 100 includes an elongate foot member 110. In the illustrated embodiment, the foot member 110 is an upper foot member, and the foot 100 further includes a heel member 120. The illustrated foot member 110 is substantially J-shaped and extends from a proximal end 112 located approximately at the location of the ankle of a natural human foot downward and forward to a toe end 114. A distal or forward end of the heel member 120 is coupled to the foot member 110 between the proximal end 112 and the toe end 114 with a portion of an upper surface of the heel member 120 facing and/or contacting a portion of a lower surface of the foot member 110, and the heel member 120 extends rearwardly from the forward end to a heel end 124. In the illustrated embodiment, the foot 100 further includes an attachment adapter 102 coupled to the proximal end 112 of the foot member 110. The attachment adapter 102 can include a connector, such as pyramid connector 104, for attaching the foot 100 to a user's residual limb or another prosthetic component. Other configurations of attachment adapters and/or connectors can also be used with the feet described herein.

In some embodiments, the foot member 110 is constructed of a resilient material capable of flexing in multiple directions. The foot member 110 can include multiple layers or laminae. Examples of possible materials for the foot member 110 include carbon, any polymer material, and any composite of polymer and fiber. The polymer can be thermoset or thermoplastic. In a composite, the fiber reinforcement can be any type of fiber, such as carbon, glass, or aramid. The fibers can be long and unidirectional, or they can be chopped and randomly oriented. In some embodiments, the heel member 120 is constructed similarly to the foot member 110.

In some embodiments, the foot member 110 includes a split 116 that at least partially extends substantially along the longitudinal axis of the foot member 110, as shown in FIGS. 1A and 1B. The heel member 120 can also include a split 126 that at least partially extends substantially along the longitudinal axis of the heel member 120, as shown in FIG. 1C. The splits 116, 126 allow medial and lateral portions of the foot member 110 and heel member 120 to flex at least partially independently of each other. The split 116 can begin in a rounded fillet, hole, or opening (for example, hole 118 shown in the embodiment of FIG. 8B). The hole 118 can help prevent the formation of stress concentrations in that region. In other embodiments, the foot member 110 and/or heel member 120 do not include splits.

The foot member 110 includes a tongue portion 130 as shown in FIGS. 1A-1C. The tongue portion 130 is defined or formed by a slot, groove, or slit 132 in the foot member 110 that extends through the entire thickness of the foot member 110 from a top or front surface 111 of the foot member 110 to a bottom or back surface 113 of the foot member 110. Optionally, the slot 132 can be a generally U-shaped slot 132. The tongue portion 130 extends longitudinally along a central axis of the foot member 110. As shown, the base 134 or curved portion of the slot 132 is positioned in a generally vertical portion of the foot member 110, and the arms 136a, 136b or straight portions of the slot 132 extend distally or forward toward the toe end 114. In the illustrated embodiment, the arms 136a, 136b extend parallel or generally parallel to one another and to a longitudinal axis of the foot member 110 along at least a portion or a majority of their length. In some embodiments, the distal ends of the arms 136a, 136b include segments 137a, 137b that extend outwardly (relative to the longitudinal axis of the foot member 110) at an angle relative to the remainder of the arms 136a, 136b, for example as shown in FIGS. 1A and 1B. Advantageously, the tongue portion 130 can move relative to the rest of the foot member 110, and movement of the tongue portion 130 relative to the rest of the foot member 110 can be selectively varied, as discussed further below, to vary the stiffness of the foot 100 during one or both of dorsiflexion and plantarflexion.

In some embodiments, the arms 136a, 136b and/or angled segments 137a, 137b terminate in rounded fillets or openings 138 as illustrated. The openings 138 can advantageously help reduce or prevent the formation of stress concentrations in that region. In some embodiments, the openings 138 also or alternatively receive fasteners (e.g., bolts, screws, or the like) that couple the heel member 120 to the foot member 110. In other embodiments, the foot member 110 includes holes 139 configured to receive fasteners that are separate from the openings 138 (for example as shown in FIG. 4A). In the embodiment illustrated in FIGS. 1A-1C, the slot 132 is symmetrical about the central longitudinal axis of the foot member 110 and the arms 136a, 136b have equal lengths. However, in other embodiments, the slot 132 may be asymmetrical. In some embodiments, a width of the tongue portion 130 can be about one-third to about one-half of a width of the foot member 110. In other embodiments, the width of the tongue portion 130 can be less than a third or more than a half of the width of the foot member 110.

In the illustrated embodiment, the foot member 110 is monolithic and the tongue portion 130 is integrally formed with the remainder of the foot member 110 and made of the same material as the rest of the foot member 110. However, in other embodiments, the tongue portion 130 is made of a different material than the rest of the foot member 110. In some such embodiments, the material for the tongue portion 130 can be incorporated into the molding process for the foot member 110 such that the foot member 110 is monolithic. Alternatively, the tongue portion 130 can be formed separately and coupled to the foot member 110. In some embodiments, the tongue portion can be made of a metal, polymer, plastic, or a fiber composition such as Spectra, Dacron, Kevlar, etc.

In use, the tongue portion 130 and portions of the foot member 110 surrounding the tongue portion 130 can flex relative to each other. This can increase the flexibility of the foot member 110. In some embodiments, the foot 100 includes a mechanism that allows the user or a prosthetist to adjust the direction and/or degree of stiffness and/or flexibility of the foot member 110.

In the embodiment illustrated in FIGS. 1A-1C, the foot 100 includes two engagement members 140a, 140b coupled to or disposed adjacent the tongue portion 130. As shown, a first engagement member 140a is coupled to or disposed on a front side 131 of the tongue portion 130, and a second engagement member 140b is coupled to or disposed on a back side 133 of the tongue portion 130. In the illustrated embodiment, the engagement members 140a, 140b are semi-circular tabs and positioned with the flat portion facing the foot member 110, although other shapes and configurations are also possible. In some embodiments, a post extends through the hole 118 and extends between and couples the front engagement member 140a and back engagement member 140b. In embodiments not including a split, the post can extend through an aperture 160 formed near the proximal end of the tongue portion 130, for example as shown in FIG. 4A. Although the illustrated embodiment includes a front engagement member 140a and a back engagement member 140b, in other embodiments, the foot 100 may include only a front engagement member 140a or only a back engagement member 140b. The front engagement member 140a and back engagement member 140b can be rotated relative to each other and to the foot member 110 and can be positioned vertically, like the front engagement member 140a as shown in FIG. 1A, or horizontally, like the back engagement member 140b as shown in FIG. 1C.

Figure 2B:
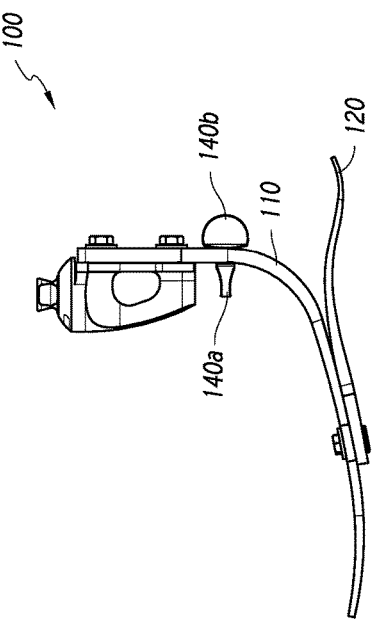

When the engagement members 140a, 140b are positioned vertically, the engagement members 140a, 140b do not extend beyond the width of the tongue portion 130. When the engagement members 140a, 140b are positioned horizontally, the engagement members 140a, 140b extend across the tongue portion 130, arms 136a, 136b of the slot 132, and portions of the foot member 110 adjacent the slot 132. The engagement members 140a 140b can be adjusted to adjust the flexibility and/or stiffness of the foot member 110. If both engagement members 140a, 140b are positioned vertically as shown in FIG. 2A, the tongue portion 130 is disconnected from the foot member 110 such that the tongue portion 130 and the rest of the foot member 110 can flex at least somewhat or partially independently of each other during use. This makes the foot member 110 more flexible when it moves in the plantarflexion and dorsiflexion direction because less of the foot member 110 is flexed (e.g., the tongue portion 130 does not contribute to the spring resistance provided by the foot member 110 during flexion); that is, the tongue portion 130 is operably disconnected from the rest of the foot member 110. If both engagement members 140a, 140b are positioned horizontally as shown in FIG. 2B, the tongue portion 130 is operably connected to the rest of the foot member 110 because contact between the outer edges or portions of the engagement members 140a, 140b and portions of the foot member 110 adjacent the slot 132 inhibits or prevents the tongue portion 130 from moving away from alignment with the rest of the foot member. The tongue portion 130 therefore flexes with the rest of the foot member 110, making the foot member 110 stiffer or less flexible when moved in plantarflexion and dorsiflexion.

Figure 2C:
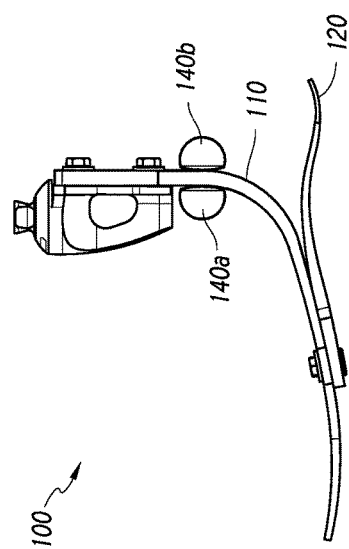

If the front engagement member 140a is positioned vertically and the back engagement member 140b is positioned horizontally as shown in FIG. 2C, the tongue member 130 is operably disconnected from the rest of the foot member 110 during dorsiflexion, but operably connected to the rest of the foot member 110 during plantarflexion. As the foot begins plantarflexing upon heel strike, the toe end 114 begins moving forward and away from the proximal end 112 coupled to the user's residual limb or another prosthetic component. As the tongue portion attempts to move forward with the toe end 114, the outer portions of the horizontal back engagement member 140b contact the portions of the foot member 110 adjacent the slot 132 and prevent or inhibit the tongue portion 130 from moving forward away from the rest of the foot member 110. Therefore, the stiffness of the foot member 110 during plantarflexion is provided by the resistance to flexion of the tongue member 130 in combination with that of the rest of the foot member 110. As the foot dorsiflexes when approaching toe off, the proximal end 112 of the foot member moves forward and toward the toe end 114 of the foot member 110 in contact with the ground. The vertical front engagement member 140a does not contact the rest of the foot member 110 and allows the rest of the foot member 110 to move forward without the tongue portion 130. That is, as the foot member 110 dorsiflexes, the tongue member 130 is operably disconnected from the rest of the foot member 110 and does not flex, so that the tongue member 130 does not contribute to the stiffness or resistance to flexion of the rest of the foot member 110 during dorsiflexion. This arrangement makes the foot member 110 relatively stiffer during heel strike and/or plantarflexion following heel strike (in other words, the foot 100 has a stiff heel) and relatively more flexible during dorsiflexion approaching and/or during toe off (the foot 100 has a soft toe).

Figure 2D:
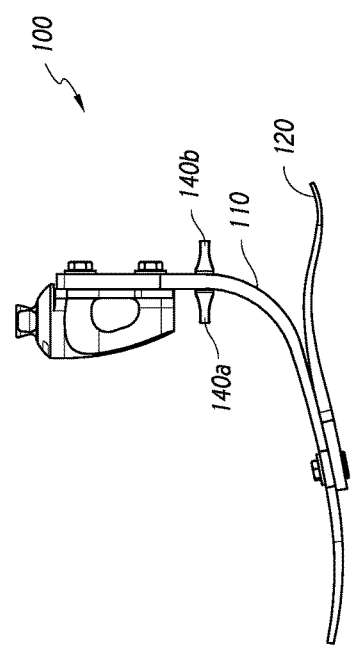

Conversely, if the front engagement member 140a is positioned horizontally and the back engagement member 140b is positioned vertically as shown in FIG. 2D, the tongue member 130 is operably connected to the rest of the foot member 110 during dorsiflexion and operably disconnected from the rest of the foot member 110 during plantarflexion. This arrangement therefore makes the foot member 110 relatively more flexible during heel strike and/or plantarflexion following heel strike (the foot has a soft heel) and relatively stiffer during dorsiflexion, such as during toe off (the foot 100 has a stiff toe). Such a configuration can advantageously provide both a dampening function (i.e., if the tongue portion 130 is allowed to flex at least somewhat independently of the rest of the foot member 110 at heel strike) and an energy return function (i.e., if the tongue portion 130 is operably connected to the rest of the foot member 110 when the foot member 110 is fully dorsiflexed just prior to initiating toe off).

The front 140a and rear 140b engagement members allow the user or a prosthetist to adjust the foot member 110 to be either relatively stiff or relatively flexible during dorsiflexion and/or plantarflexion. The tongue portion 130 can be either operably connected or disconnected from the rest of the foot member 110 in dorsiflexion and operably connected or disconnected from the rest of the foot member 110 in plantarflexion. In other embodiments, the foot member 110 includes an adjustment mechanism that allows for adjustment of the degree to which the tongue portion 130 is engaged with or operably connected to the foot member 110. Such a mechanism provides for greater variability in the range of stiffness and/or flexibility to which the foot member 110 can be adjusted.

Figure 3:
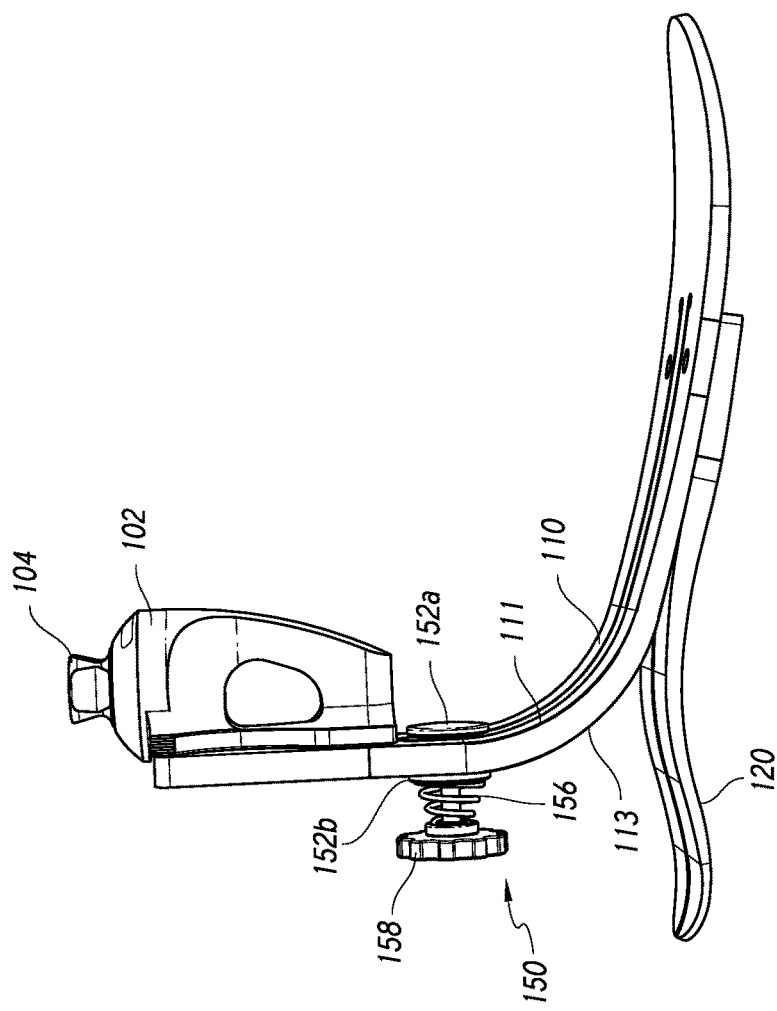
FIG. 3 illustrates an example embodiment of a prosthetic foot having a spring mechanism for adjusting stiffness.

For example, FIGS. 3-4C illustrate an example embodiment of a foot member 110 including a spring adjustment mechanism 150. As shown in FIG. 4C, the spring adjustment mechanism 150 includes shaft 154, a flange 152a at a first end of the shaft 154, an adjustment knob 158 at a second end of the shaft 154, a washer 152b slidably positioned on the shaft 154 between the first flange 152a and adjustment knob 158 (in other words, the washer 152b can translate along the shaft 154, and a spring 156 extending between and coupled to the washer 152b and adjustment knob 158). The shaft 154 of the spring adjustment mechanism 150 extends through the aperture 160 of the tongue portion, the flange 152a is disposed adjacent or positioned against the front side 111 of the foot member 110 and front side 131 of the tongue portion 130, and the washer 152b is disposed on the back side 113 of the foot member 110 and back side 133 of the tongue portion 130, as shown in FIG. 4B. In some embodiments in which the foot member 110 includes a split 132 beginning in a hole 118, for example as shown in FIG. 9, the shaft 154 extends through the hole 118.

In the illustrated embodiment, the flange 152a contacts portions of the foot member 110 adjacent the slot 132 when the foot dorsiflexes such that the tongue 130 is operably connected to the rest of the foot member 110 in dorsiflexion. In some embodiments, the spring 156 biases the washer 152b against the back of the foot member 110. Because the washer 152b can slide along the shaft 154 as the spring compresses and relaxes, the tongue portion 130 can move independently of the rest of the foot member 110 to some extent when the foot plantarflexes. The adjustment knob 158 can be rotated in a first direction to compress the spring 156 and the opposite direction to relax the spring 156 (e.g., to gradually vary a stiffness of the foot member 110). As the degree or amount of compression of the spring 156 increases (e.g., due to rotation of the knob 158), the range of motion of the washer 152b along the shaft 154 decreases, and the tongue portion 130 becomes more operably connected to the rest of the foot member 110, making the foot member 110 stiffer or less flexible in plantarflexion.

Although in the illustrated embodiment the spring 156 and adjustment knob 158 are positioned on the back of the foot member 110, in other embodiments, the orientation of the spring adjustment mechanism 150 can be reversed such that the spring 156 and adjustment knob 158 are positioned on the front of the foot member 110. In such an embodiment, the flange 152a contacts portions of the foot member 110 adjacent the slot 132 when the foot plantarflexes such that the tongue portion 130 is operably connected to the rest of the foot member 110 in plantarflexion, but the washer 152b can slide along the shaft 154 during dorsiflexion so that the tongue portion 130 can be operably disconnected from the rest of the foot member 110 during at least a portion of dorsiflexion.

FIGS. 5-6C illustrate another embodiment of a spring adjustment mechanism 170 including two springs. In the illustrated embodiment, the adjustment mechanism 170 includes a shaft 174, an adjustment knob 178 coupled to one end of the shaft 174 and disposed behind the foot member 110, a flange 172a coupled to the other end of the shaft 174 and disposed in front of the foot member 110, a front washer 172b slidably disposed on the shaft 174 in front of the foot member 110, a back washer 172c slidably disposed on the shaft 174 behind the foot member 110, a front spring 176b extending between and coupled to the flange 172a and the front washer 172b, and a back spring 176a extending between and coupled to the back washer 172c and the adjustment knob 178. In other embodiments, the adjustment mechanism 170 can be reversed such that the flange 172a is positioned behind the foot member 110 and the adjustment knob 178 is positioned in front of the foot member 110. The two spring configuration can advantageously allow the adjustment mechanism 170 and therefore the stiffness of the foot member 110 to be tuned with more sensitivity compared to a one-spring adjustment mechanism. The two slidable washers 172b, 172c in the two spring configuration allow the tongue portion 130 to be operably disconnected from and move relative to the rest of the foot member 110 during at least a portion of both dorsiflexion and plantarflexion.

Spring adjustment mechanisms such as mechanisms 150, 170 shown in FIGS. 3-6C advantageously allow the flexibility of the foot member 110 to be adjusted or tuned with greater variability compared to the adjustment mechanism shown in FIGS. 1A-2D and described herein (that is, with a spring mechanism the flexibility can be adjusted over a range of degrees of flexibility or stiffness, whereas the adjustment mechanism of FIGS. 1A-2D generally allows for selection between two degrees of flexibility in dorsiflexion and two degrees of flexibility in plantarflexion). However, with the spring adjustment mechanism 170 having a single adjustment knob 178, the stiffness or flexibility of the foot member 110 in both dorsiflexion and plantarflexion are controlled or adjusted together, whereas the adjustment mechanism of FIGS. 1A-2D allows the stiffness or flexibility in dorsiflexion to be adjusted independently of that in plantarflexion.

FIGS. 7A and 7B illustrate an alternative spring adjustment mechanism 180 including front 186b and back 186a springs as well as front 188b and back 188a adjustment knobs. This configuration advantageously allows for independent control and adjustment of each spring and therefore independent control and adjustment of the flexibility of the foot member 110 during dorsiflexion and plantarflexion. The front spring 186b and front adjustment knob 188b control or adjust the stiffness or flexibility of the foot member 110 in dorsiflexion, and the back spring 186a and back adjustment knob 188a control or adjust the stiffness or flexibility of the foot member 110 in plantarflexion.

Although mechanical engagement member and spring type adjustment mechanisms have been shown and described herein, other adjustment mechanisms are also possible to control movement of the tongue portion 130 relative to the remainder of the foot member 110. For example, the spring mechanism 150, 170 can be replaced with hydraulic, pneumatic, or motorized adjustment mechanisms. The spring mechanisms 150, 170 can also be replaced with other mechanical adjustment mechanisms, for example, including components or inserts made of rubber, elastic, polymers, or other materials.

Figure 8A:
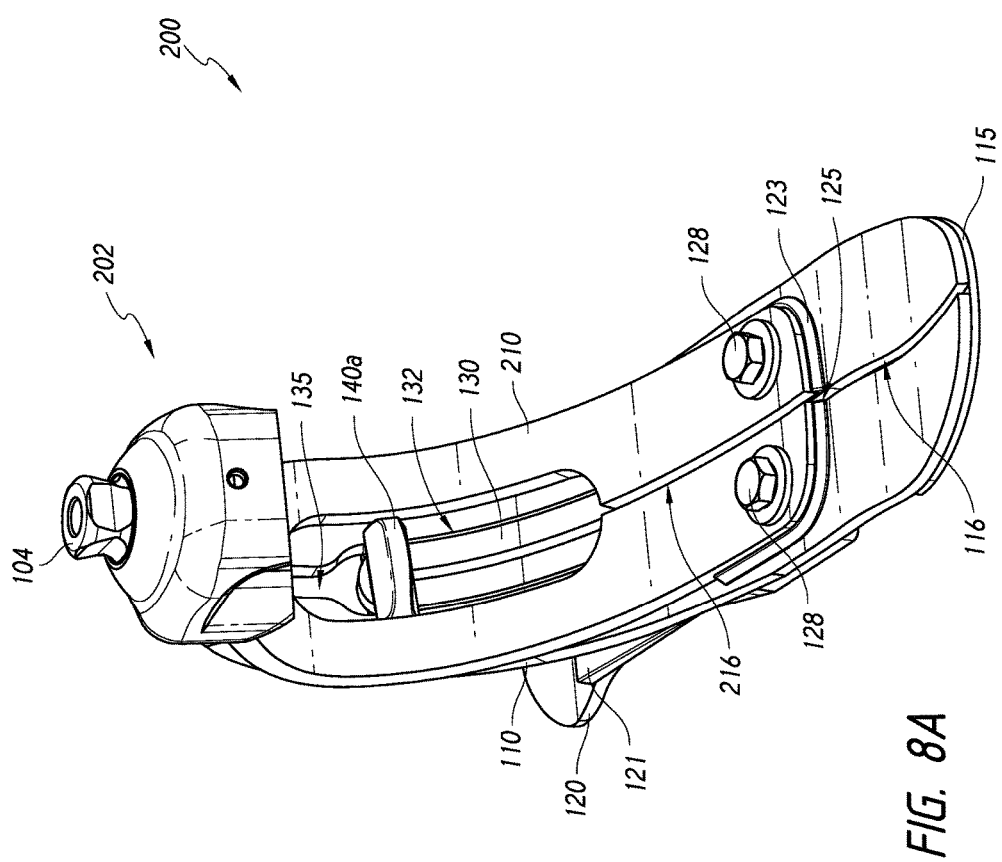
FIG. 8A illustrates another example embodiment of a prosthetic foot including the mechanism for adjusting stiffness of FIGS. 1A-3D.
Figure 8B:
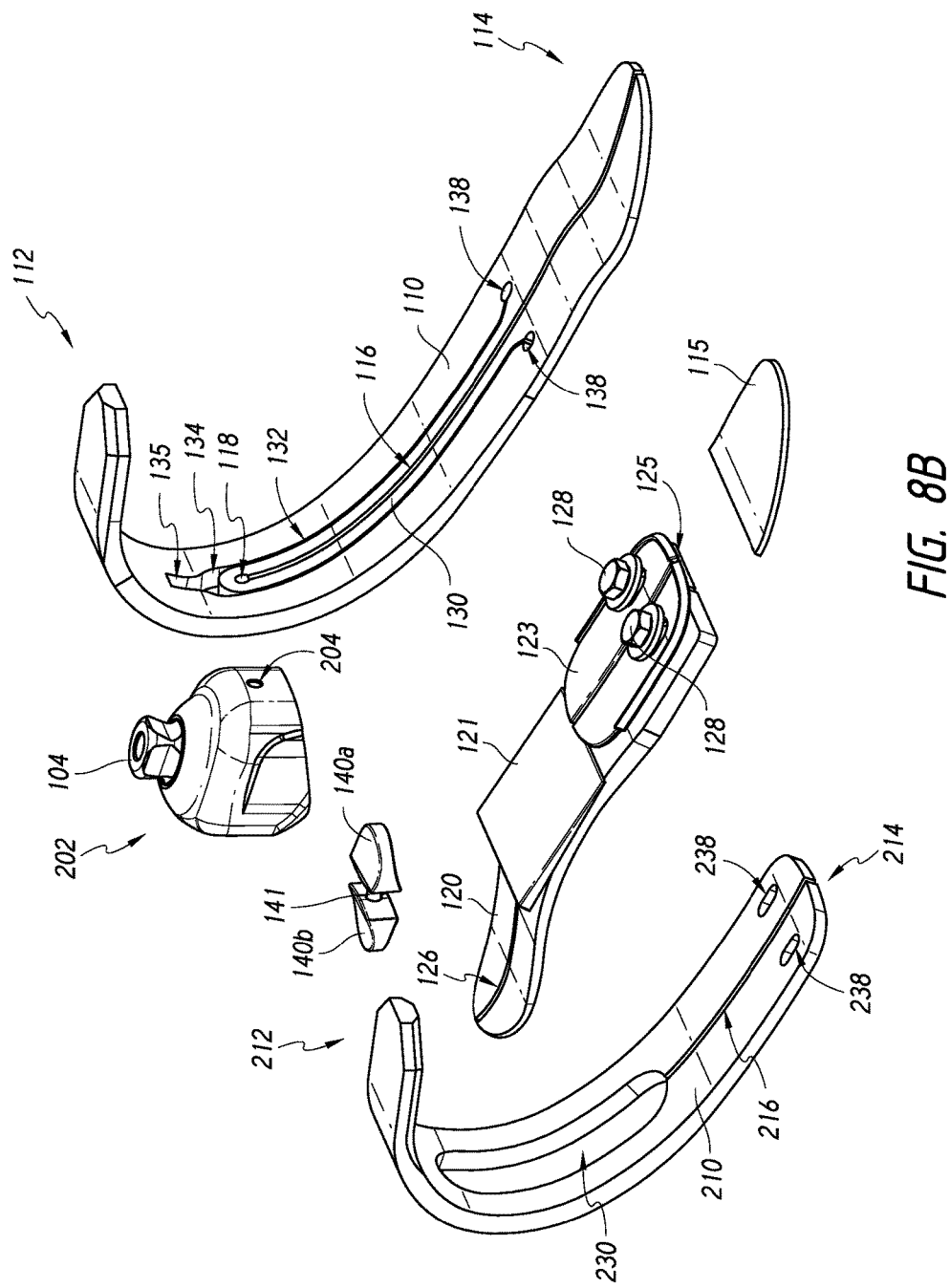
FIG. 8B illustrates an exploded view of the prosthetic foot of FIG. 8A.

The adjustment mechanisms shown and described herein, and other adjustment mechanisms according to the present disclosure, can also be incorporated into prosthetic feet having other configurations. For example, FIGS. 8A-8B illustrate another example embodiment of a prosthetic foot 200 incorporating foot member 110 and front 140a and back 140b engagement members. In the illustrated embodiment, the prosthetic foot 200 also includes a heel member 120, an upper foot member 210, and an adapter 202 including a pyramid connector 104. However, in other embodiments, the foot 200 does not include the upper foot member 210. In this embodiment, the foot member 110 is generally C-shaped such that the foot member 110 extends from a generally horizontal proximal end 112 to a generally horizontal toe end 114 and includes a generally forwardly-facing concave curved portion between the proximal end 112 and the toe end 114. The upper foot member 210 is disposed generally above the foot member 110 and is also generally C-shaped. The upper foot member 210 extends from a generally horizontal proximal end 212 to a toe end 214. In the illustrated embodiment, the upper foot member 210 is shorter than the foot member 110 such that the toe end 214 of the upper foot member 210 is proximal to the toe end 114 of the foot member 110. The upper foot member 210 can include a split 216 extending along at least a portion of a longitudinal axis of the upper foot member 210. The proximal ends 112, 212 of the foot member 110 and upper foot member 212 are received in a rearwardly facing cavity of the adapter 202. In some embodiments, the proximal ends 112, 212 of the foot member 110 and upper foot member 212 can be secured to the adapter 202 and/or each other with a curable material, for example, epoxy. The adapter 202 can include one or more inlet holes 204 that are in fluid communication with the rearwardly facing cavity of the adapter 202 so that the inlet holes 204 can serve as injection points for the introduction of the curable material to the cavity. Additional details on features of prosthetic feet and adapters having configurations similar to prosthetic foot 200 and adapter 202 can be found in U.S. Publication No. 2013/0144403, entitled "Prosthetic Foot with Dual Foot Blades and Vertically Offset Toe," the entirety of which is hereby incorporated by reference herein and should be considered a part of this specification.

In the illustrated embodiment, a crepe portion 115 is attached to the underside of the toe end 114 of the foot member 110. As shown, the crepe portion 115 can be aligned with the toe end 114 of the foot member 110 so as to not extend past the toe end 114. Preferably, the crepe portion 115 comprises a resilient pad or cushion. For example, the crepe portion 115 can be made of a compressible material. The crepe portion 115 can also be made of a porous material. In some embodiments, the crepe portion 115 can be made of solid urethane. In one preferred embodiment, the crepe portion 115 is attached to the toe end 114 of the foot member 110 with an adhesive. However, other attachment means can be used, such as bolts, screws, and bands wrapped around the crepe portion 115 and the foot member 110. The crepe portion 115 is preferably configured to have a shape corresponding to the shape of the foot member 110. For example, the crepe portion 115 can have a rounded edge corresponding to the rounded distal edge of the toe end 114. In the illustrated embodiment, the crepe portion 115 has a uniform thickness. In another preferred embodiment, the crepe portion 115 can have a varying thickness. For example, the crepe portion 115 can have a decreasing thickness in the direction of the distal end of the foot member 110. In other preferred embodiments, the foot member 110 does not have a crepe portion 115 attached to it, so that the toe end 114 of the foot member 110 operatively contacts the support surface.

In the embodiment shown in FIGS. 8A-8B, the upper foot member 210, foot member 110, and heel member 120 are coupled via fasteners 128 (e.g., bolts, screws, or the like) that extend through the openings 138 in the foot member 110, corresponding openings 238 near the toe end 214 of the upper foot member 210, and corresponding openings near the forward end of the heel member 120. In the illustrated embodiment, the prosthetic foot 200 includes a resilient member 121, such as a wedge, disposed between the heel member 120 and the foot member 110. The resilient member 121 can separate at least a portion of the foot member 110 from the heel member 120. In some embodiments, the resilient member can completely separate the foot member 110 from the heel member 120. The resilient member 121 can be removably disposed between the heel member 120 and foot member 110 or fixed between the heel member 120 and foot member 110, e.g., with an adhesive, bolts, or screw. The resilient member 121 can provide shock absorption to the prosthetic foot 200. In some embodiments, the resilient member 121 can be made, for example, of a hard plastic, such as polyurethane or polypropylene. The resilient member 121 can also be made of a more compressible material, such as foam, natural or synthetic rubbers, or the like. However, the resilient member 121 can be made of any material that provides adequate shock absorption. In some embodiments, a spacer 123 is disposed between a portion of the foot member 110 and the upper foot member 210 proximate the toe end 214 of the upper foot member 210. In some embodiments, the spacer 123 creates a gap between the foot member 110 and the upper foot member 210. The spacer can advantageously provide noise reduction during operation of the prosthetic foot 200, for example, to reduce noise due to friction between the foot member 110 and upper foot member 210 when the members 110, 210 contact each other. In the illustrated embodiment, the spacer 123 has a longitudinal split 125 that is aligned with the splits 116, 216, 126 in the foot member 110, upper foot member 210, and heel member 120, respectively.

As shown, the upper foot member 210 includes an opening 230 extending along a portion of the upper foot member 210. In the illustrated embodiment, the split 216 extends from the opening 230 to the toe end 214, although in other embodiments, the split 216 may not extend to the opening 230 or to the toe end 214. The opening 230 is wide enough to accommodate the front engagement member 140a when turned horizontally, as shown in FIG. 8A. In the illustrated embodiment, the foot member 110 includes an aperture extension 135 extending upwardly or proximally from the base 134 of the slot 132. The aperture extension 135 can be sized to accommodate the front engagement member 140a when turned vertically.

In some alternative embodiments, the prosthetic foot 200 includes a spring adjustment mechanism as described herein. In other embodiments including either the mechanical engagement member adjustment mechanism or a spring adjustment mechanism, the foot member 110 may have a low profile shape in which the toe end is generally horizontally oriented and a proximal section is inclined at an angle relative to the toe end and relative to a support surface. The foot member 110 can also be incorporated into various other configurations of prosthetic feet.

Figure 9B:
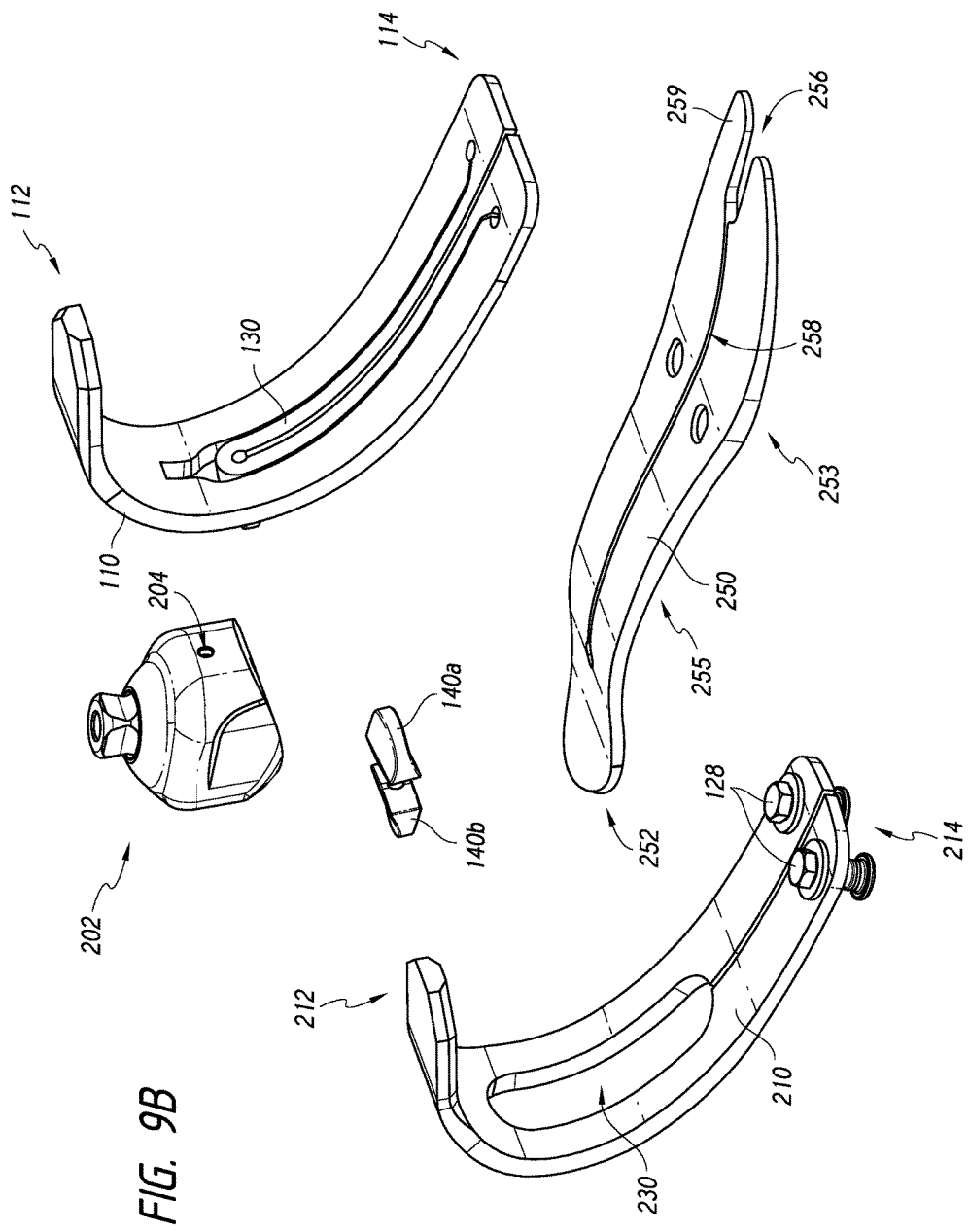
FIG. 9B illustrates an exploded view of the prosthetic foot of FIG. 9A.

FIGS. 9A-9B illustrate another example embodiment of a prosthetic foot 200'. Prosthetic foot 200' is similar to prosthetic foot 200. However, in prosthetic foot 200', the foot member 110 is approximately the same length as, or does not extend significantly distal to the toe end 214 of, the upper foot member 210. Instead of heel member 120, prosthetic foot 200' includes a lower foot member 250 that extends from a heel end 252 to a toe end 254. Additional details on features of lower foot members and prosthetic feet having configurations similar to prosthetic foot 200' can be found in U.S. application Ser. No. 14/755,464, entitled "Prosthetic Feet and Foot covers," the entirety of which is hereby incorporated by reference herein and should be considered a part of this specification.

In some embodiments, a forefoot region 253 of the lower foot member 250 is wider than an arch region 255 and/or a heel region 251 of the foot member 250. The forefoot region 253 can be wider than a forefoot region of previously available prosthetic feet. For example, in some previously available prosthetic feet, the ratio of the width of the forefoot region to the length of the foot element is about 25-26%. In some prosthetic feet according to the present disclosure, the ratio of the width of the forefoot region 253 to the length of the foot element is about 30%.

In some embodiments, a toe region 257 of the lower foot member 250 includes a generally U-shaped cut-out portion, slot or gap 256 extending inwardly from the toe end 254. In some embodiments, the cut-out 256 is positioned toward a medial side of a longitudinal axis of the lower foot member 250, but is spaced from a medial edge of the lower foot member 250 (e.g., the cut-out portion or gap 256 is defined between the longitudinal axis and medial edge of the lower foot member 250). The cut-out 256 gives the lower foot member 250 a "sandal toe" appearance and/or function and defines a structural "big toe" 259. The cut out portion 256 can receive a strap of a sandal. Because the forefoot region 253 is wider than a remainder of the foot element and wider than previously available prosthetic feet, the cut-out 256 and big toe 259 can be offset from the longitudinal axis of the lower foot member 250 to a greater extent. In the illustrated embodiment, the big toe 259 is longer (e.g., extends further distally) than the remaining "toes" or the remainder of the toe portion 257. This can advantageously provide the lower foot member 250 with a full length toe lever and allow the lower foot member 250 to more closely approximate or mimic a natural human foot during rollover. The cut-out portion 256 can provide the toe region 257 of the lower foot member 250 with a lesser stiffness on the medial side, which can help guide the center of mass of the foot 200' toward the medial side during rollover.

In some embodiments, the lower foot member 250 includes a split 258 that at least partially separates the lower foot member 250 into a medial portion and a lateral portion. In the illustrated embodiment, the split 258 does not extend to the heel end 252 of the lower foot member 250. In the illustrated embodiment, the slit 258 extends substantially straight from a proximal end (or end of the split 258 closest to the heel end 252) through the arch region 255, then curves medially in the forefoot region 253 or approximately at a border between the arch region 255 and the forefoot region 253 and extends to the cut out 256. However, other configurations for the split 258 are also possible. For example, in other embodiments, the split 258 can be entirely straight, can be entirely curved, and/or can extend to a medial or lateral edge of the lower foot member 250.

FIGS. 9C-9F illustrate an example embodiment of a lower foot member 250 that includes a drop-toe or vertically offset toe portion. In the illustrated embodiment, a forefoot piece 260 is coupled, either permanently or removably, to a bottom surface of at least a portion of the forefoot region 253 and/or toe region 257 of the lower foot member 250. In some embodiments, the forefoot piece 260 is made of a hard plastic, such as polyurethane or polypropylene. The forefoot piece 260 can also be made of a more compressible material, such as foam, natural or synthetic rubbers, or the like. Other materials are also possible. As shown in the illustrated embodiment, the bottom surface of the forefoot region 253 and toe region 257 can be flattened or straight (rather than curved) to accommodate a forefoot piece 260 having a flat or straight upper surface. In other embodiments, the bottom surface of the forefoot region 253 and toe region 257 can be curved or partially curved to accommodate a forefoot piece 260 having a curved or partially curved upper surface. As shown, the forefoot piece 260 is generally sized and shaped to correspond to the forefoot region 253 and/or toe region 257 of the lower foot member 250, and a distal end of the forefoot piece 260 can include a cut-out 266 that corresponds in shape and size to the cut-out 256 of the lower foot member 250.

In the illustrated embodiment, a bottom surface of the forefoot piece 260 is curved or downward-facing convex. In some embodiments, the bottom surface of the forefoot piece 260 has a curvature that is discontinuous relative to and/or different from the curvature of the lower surface of the lower foot member 250 proximal to the forefoot piece 260. The bottom surface of the forefoot piece 260 may therefore be downwardly vertically offset from a remainder of the lower foot member 250 proximal to the forefoot piece 260. The forefoot piece 260 can advantageously allow for the lower foot member 250 to be supported during stance at portions of the heel and toe regions rather than at the heel and fasteners 128 that couple other foot elements, such as foot member 110 and upper foot member 210, to the lower foot member 250. This allows for enhanced suspension and increased vertical displacement of the lower foot member 250 during stance because the fasteners are not in contact with the ground.

FIGS. 10-13 illustrate an example embodiment of a prosthetic foot 300 including another mechanism for adjusting stiffness and/or flexibility. The foot 300 includes a lower foot member 320, an upper foot member 310, an attachment adapter 330 having a pyramid connector 104, and a C-member 340. In the illustrated embodiment, the lower foot member 320 extends from a heel end 322 to a toe end 324, and the upper foot member 310 has a substantially C-shape extending from a proximal end 312 coupled to the attachment adapter 330 to a distal end 314 that is coupled to the lower foot member 320 proximal to or rearward of the toe end 324. In the illustrated embodiment, the upper foot member 310 includes a split 317 extending through a portion of the upper foot member 310. In other embodiments, the upper foot member 310 can extend to a toe end, and the foot 300 can include a heel member, for example, similar to heel member 120, rather than the lower foot member 320.

Figure 10:
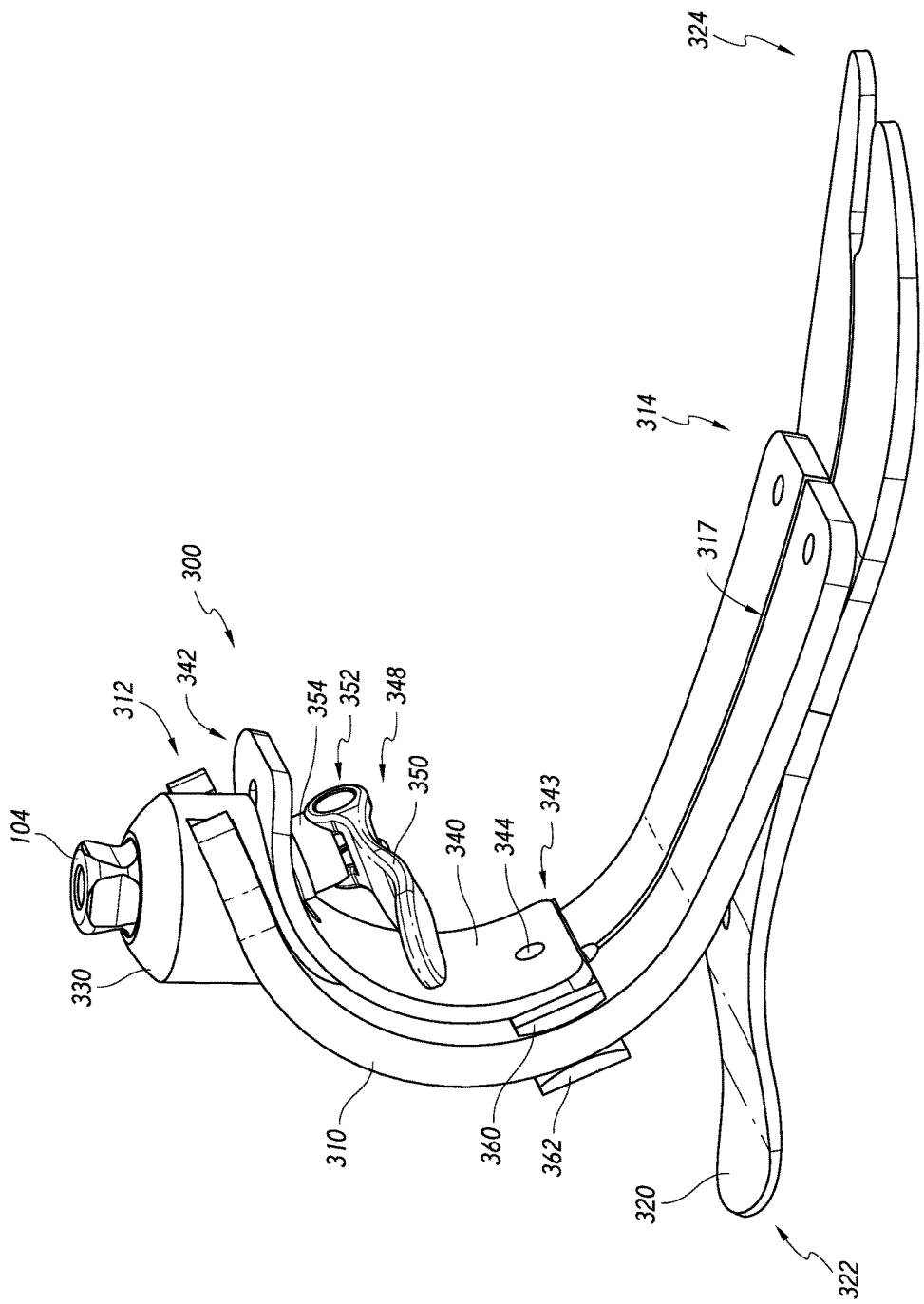
FIGS. 10-13 illustrate various views of another example embodiment of a prosthetic foot having a mechanism for adjusting stiffness.
Figure 11:
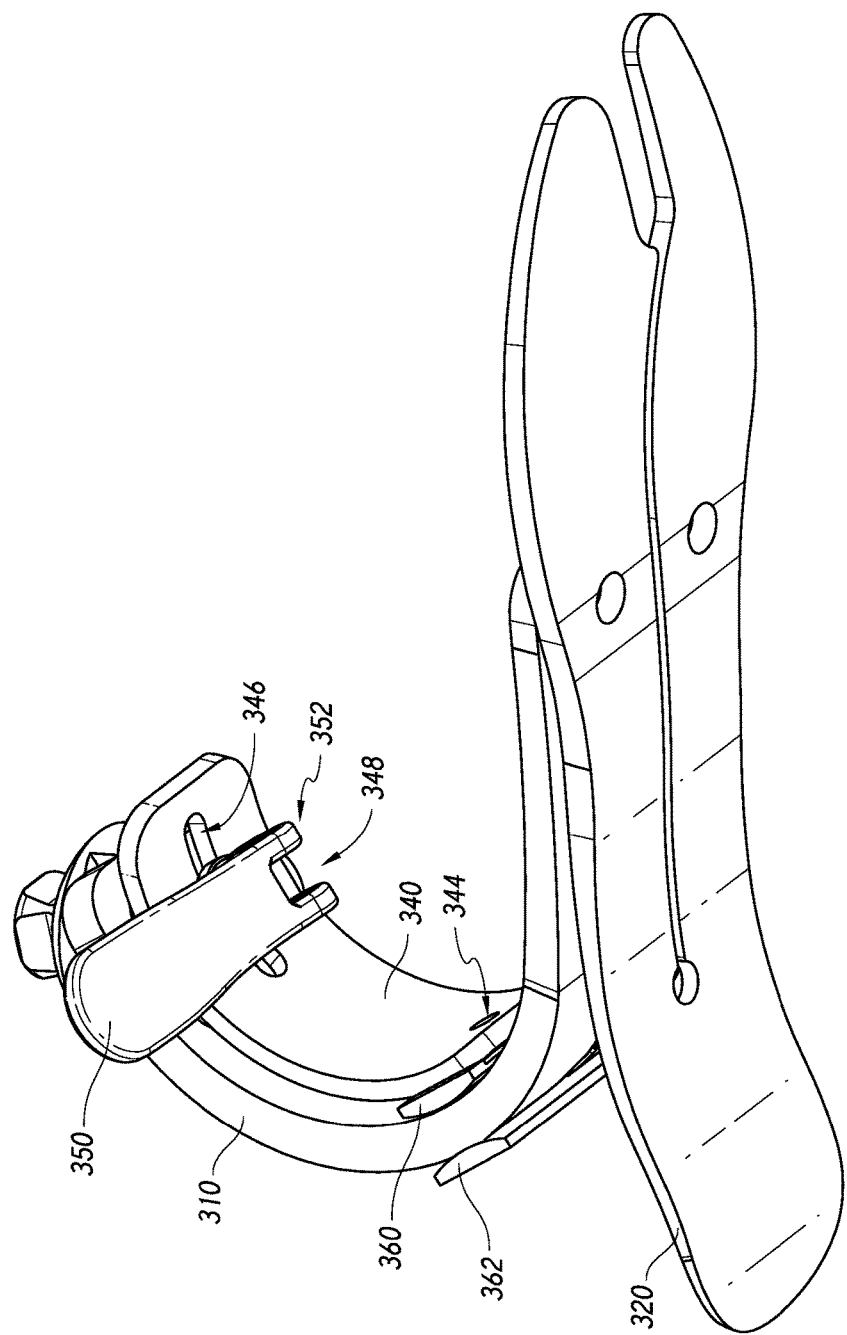
Figure 12:
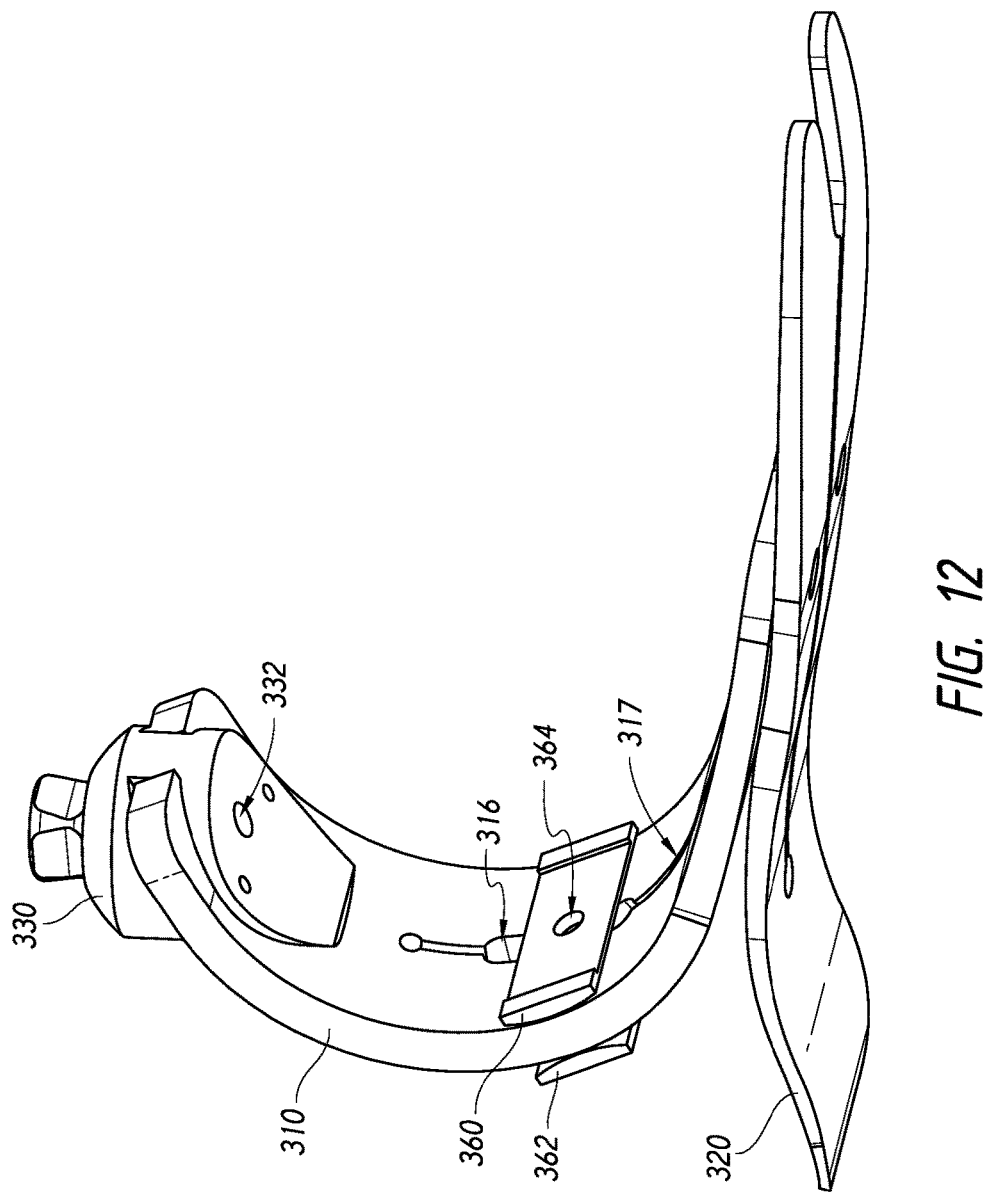
Figure 13:
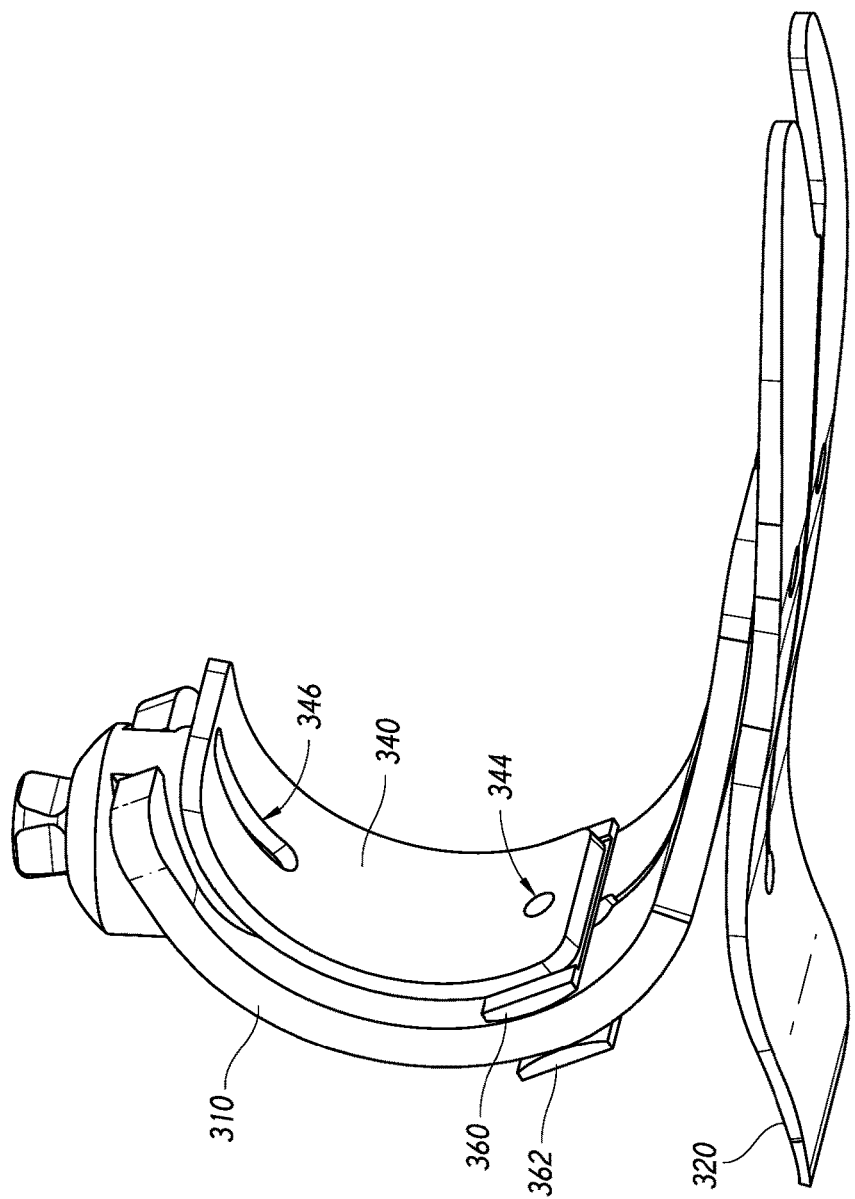

The C-member 340 is positioned generally in front of the upper foot member 310, and the curvature of the C-member 340 generally corresponds to that of the upper foot member 310. In the illustrated embodiment, a spacer 360 is positioned between a distal or lower end 343 of the C-member 340 and the upper foot member 310. As shown, the foot 300 can include a second spacer 362 disposed on the opposite (back) side of the foot member 310 from the first spacer 360. The C-member 340 includes an aperture 344 at or near the distal end 343 and a slot 346 near an upper or proximal end 342 as shown in FIGS. 10-11 and 13. The upper foot member 310 includes a slot 316 as shown in FIG. 12. In the illustrated embodiment, the split 317 extends from the slot 316 to the distal end 314 of the upper foot member 310. A lower surface of the attachment adapter 330 includes an aperture 332 as shown in FIG. 12.

In some embodiments, C-member 340 can be releasably coupled to the upper foot member 310 via a fastener that extends through the aperture 344 of the C-member 340, an aperture 364 in the first spacer 360, the slot 316 of the upper foot member 310, and an aperture in the second spacer 362. In the illustrated embodiment, the C-member 340 is also releasably coupled to the attachment adapter 330 via an adjustment assembly 348. The adjustment assembly 348 includes a body portion 354 and a handle 350 pivotally or hingedly coupled to the body portion 354 at pivot 352. The body portion 354 includes a post that extends through the slot 346 of the C-member 340 and into the aperture 332 of the attachment adapter 330. When the handle 350 is positioned extending laterally as shown in FIG. 10, the body portion 354 applies pressure to the C-member 340 to lock the C-member 340 against the attachment adapter 330.

During ambulation, the gap between the upper foot member 310 and C-member 340 closes as the foot moves from heel strike to toe off. As the gap closes, the prosthetic foot 300 becomes stiffer. To alter the stiffness characteristics of the foot 300, the position of the C-member 340 relative to the upper foot member 310 can be adjusted. To do so, the user or a prosthetist can release the fastener extending through the aperture 344, first spacer 360, upper foot member 310, and second spacer 362 and pivot the handle 350 of the adjustment assembly 348 away from the upper foot member 310 to unlock the C-member 340 from the attachment adapter 330. The user or prosthetist can then slide the C-member 340 along the upper foot member 310 so that the fastener extending through the aperture 344, first spacer 360, upper foot member 310, and second spacer 362 travels in the slot 316, and the first 360 and second 362 spacers slide or move relative to the upper foot member 310 along with the distal end 343 of the C-member 340. Simultaneously, the post of the body portion 354 of the adjustment assembly 348 remains stationary, but the slot 346 allows the C-member 340 to move relative to the post. When the user or prosthetist has adjusted the C-member 340 to the desired position, he or she can resecure the fastener extending through the aperture 344, first spacer 360, upper foot member 310, and second spacer 362 and pivot the handle 350 of the adjustment assembly 348 back toward the upper foot member 310 to lock the C-member 340 to the attachment adapter 330.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
   an elongate foot element extending from a proximal end to a distal end, the foot element comprising a tongue portion defined by a slot in the foot element that partially separates the tongue portion from a remainder of the elongate foot element, wherein the slot extends through an entire thickness of the elongate foot element from a top surface of the elongate foot element to a bottom surface of the elongate foot element, wherein a distal end of the slot is proximal to the distal end of the elongate foot element, wherein a distal end of the tongue portion is fixed relative to the remainder of the elongate foot element, and wherein the top surface of the tongue portion is substantially coplanar with the top surface of the remainder of the elongate foot element along the entire length of the tongue portion when the prosthetic foot is at rest; and
   a mechanism configured to be selectively actuated by a user to operatively connect or operatively disconnect a proximal end of the tongue portion from the remainder of the foot element, the mechanism being coupled to the tongue portion when the tongue portion is operatively connected to and operatively disconnected from the remainder of the elongate foot element, wherein when the tongue portion is operatively connected to the remainder of the foot element the foot element exhibits relatively greater stiffness, and when the tongue portion is operatively disconnected from the remainder of the foot element the foot element exhibits relatively lower stiffness.

2. The prosthetic foot of claim 1, wherein the mechanism is configured to be selectively actuated to adjust the stiffness of the foot element in one or both of plantarflexion and dorsiflexion.

3. The prosthetic foot of claim 2, wherein the mechanism comprises first and second engagement members coupled to the tongue portion, the first engagement member disposed on a front side of the foot element and the second engagement member disposed on a back side of the foot element, wherein the first engagement member is configured to be actuated to selectively operatively connect or operatively disconnect the tongue portion from the remainder of the foot element in dorsiflexion, and wherein the second engagement member is configured to be actuated to selectively operatively connect or operatively disconnect the tongue portion from the remainder of the foot element in plantarflexion.

4. The prosthetic foot of claim 1, wherein when the tongue portion is operatively connected to the remainder of the foot element the tongue portion flexes with the remainder of the foot element, and when the tongue portion is operatively disconnected from the remainder of the foot element the tongue portion flexes at least partially independently of the remainder of the foot element.

5. The prosthetic foot of claim 4, wherein the tongue portion is configured to flex with the remainder of the foot element during one of plantarflexion and dorsiflexion and configured to flex at least partially independently of the remainder of the foot element during the other of plantarflexion and dorsiflexion.

6. The prosthetic foot of claim 1, further comprising an adapter coupled to the foot element proximate to the proximal end.

7. The prosthetic foot of claim 1, further comprising a second foot element disposed below the foot element, wherein the second foot element is coupled to the foot element by fasteners extending through openings in the foot element and the second foot element.

8. The prosthetic foot of claim 7, wherein the second foot element extends from a heel end to a toe end of the prosthetic foot.

9. The prosthetic foot of claim 1, wherein the slot is U-shaped.

10. The prosthetic foot of claim 1, wherein the elongate foot element is monolithic and the tongue portion is integrally formed with the remainder of the elongate foot element.

11. A prosthetic foot comprising:
an elongate foot element extending from a proximal end to a distal end, the foot element comprising a tongue portion defined by a slot in the foot element that partially separates the tongue portion from a remainder of the elongate foot element, wherein the slot extends through an entire thickness of the elongate foot element from a top surface of the elongate foot element to a bottom surface of the elongate foot element, wherein a distal end of the slot is proximal to the distal end of the elongate foot element, wherein a distal end of the tongue portion is fixed relative to the remainder of the elongate foot element; and
means for selectively coupling the tongue portion with the remainder of the foot element for selectively adjusting a stiffness of the elongate foot element during one or both of dorsiflexion and plantarflexion between at least two different stiffness levels wherein said means selectively operatively connects or operatively disconnects the tongue portion from the remainder of the foot element to thereby adjust the stiffness of the elongate foot element, and wherein the means is coupled to the tongue portion when the tongue portion is operatively connected to and operatively disconnected from the remainder of the elongate foot element.

12. The prosthetic foot of claim 11, wherein said means is configured to independently vary a stiffness of the foot element in dorsiflexion and plantarflexion.

13. The prosthetic foot of claim 11, wherein said means selectively adjusts the stiffness of the elongate foot element during one or both of dorsiflexion and plantarflexion, wherein when the tongue portion is operatively connected to the remainder of the foot element, the foot element exhibits relatively greater stiffness, and when the tongue portion is operatively disconnected from the remainder of the foot element, the foot element exhibits relatively lower stiffness.

14. The prosthetic foot of claim 11, wherein when the tongue portion is coupled to the remainder of the foot element the tongue portion flexes with the remainder of the foot element, and when the tongue portion is not coupled to the remainder of the foot element the tongue portion flexes at least partially independently of the remainder of the foot element.

15. The prosthetic foot of claim 14, wherein the tongue portion is configured to flex with the remainder of the foot element during one of plantarflexion and dorsiflexion and configured to flex at least partially independently of the remainder of the foot element during the other of plantarflexion and dorsiflexion.

16. The prosthetic foot of claim 11, wherein the slot is U-shaped.

17. The prosthetic foot of claim 11, wherein the elongate foot element is monolithic and the tongue portion is integrally formed with the remainder of the elongate foot element.

18. A prosthetic foot comprising:
a first elongate foot element extending from a proximal end to a distal end, the foot element comprising a tongue portion defined by a slot in the foot element that partially separates the tongue portion from a remainder of the elongate foot element, wherein a distal end of the slot is proximal to the distal end of the elongate foot element and a distal end of the tongue portion is fixed relative to the remainder of the elongate foot element, and wherein the slot is U-shaped;
a second foot element extending from a heel end to a toe end, the second foot element disposed below and coupled to the first elongate foot element, wherein the distal end of the first elongate foot element is positioned proximal of the toe end of the second foot element; and
a mechanism configured to be selectively actuated by a user to operatively connect or operatively disconnect a proximal end of the tongue portion from the remainder of the first elongate foot element, wherein when the tongue portion is operatively connected to the remainder of the first elongate foot element the first elongate foot element exhibits relatively greater stiffness, and when the tongue portion is operatively disconnected from the remainder of the first elongate foot element the first elongate foot element exhibits relatively lower stiffness.

19. The prosthetic foot of claim 18, wherein the first elongate foot element is generally C-shaped.

20. The prosthetic foot of claim 18, wherein the mechanism comprises at least one tab engagement member and wherein the tongue portion is operatively connected to the remainder of the first elongate foot element when the tab engagement member is positioned in a first orientation and the tongue portion is operatively disconnected from the remainder of the first elongate foot element when the tab engagement member is positioned in a second orientation.

21. The prosthetic foot of claim 20, wherein the at least one tab engagement member comprises two tab engagement members, a first tab engagement member disposed on a front side of the first elongate foot element and a second tab engagement member disposed on a back side of the first elongate foot element.

22. The prosthetic foot of claim 18, wherein when the tongue portion is operatively connected to the remainder of the first elongate foot element the tongue portion flexes with the remainder of the first elongate foot element, and when the tongue portion is operatively disconnected from the remainder of the first elongate foot element the tongue portion flexes at least partially independently of the remainder of the first elongate foot element.

23. The prosthetic foot of claim 22, wherein the tongue portion is configured to flex with the remainder of the first elongate foot element during one of plantarflexion and dorsiflexion and configured to flex at least partially independently of the remainder of the first elongate foot element during the other of plantarflexion and dorsiflexion.

* * * * *

UNITED STATES PATENT AND TRADEMARK OFFICE
CERTIFICATE OF CORRECTION

PATENT NO. : 10,034,782 B2
APPLICATION NO. : 14/858693
DATED : July 31, 2018
INVENTOR(S) : David Sandahl Page 1 of 1

It is certified that error appears in the above-identified patent and that said Letters Patent is hereby corrected as shown below:

In the Claims

In Column 20 at Line 5, in Claim 11, change "levels" to --levels,--.

Signed and Sealed this
Eighth Day of January, 2019

Andrei Iancu
*Director of the United States Patent and Trademark Office*